United States Patent
Tsukamoto et al.

(10) Patent No.: US 8,466,089 B2
(45) Date of Patent: *Jun. 18, 2013

(54) PYRAZOLE COMPOUNDS, PROCESS FOR THEIR PRODUCTION AND HERBICIDES CONTAINING THEM

(75) Inventors: Masamitsu Tsukamoto, Kusatsu (JP); Hiroshi Kikugawa, Kusatsu (JP); Souichiro Nagayama, Kusatsu (JP); Tatsuya Okita, Kusatsu (JP); Hiroshi Hata, Kusatsu (JP)

(73) Assignee: Ishihara Sangyo Kaisha, Ltd., Osaka-shi (JP)

(*) Notice: Subject to any disclaimer, the term of this patent is extended or adjusted under 35 U.S.C. 154(b) by 161 days.

This patent is subject to a terminal disclaimer.

(21) Appl. No.: 12/993,760

(22) PCT Filed: May 19, 2009

(86) PCT No.: PCT/JP2009/059489
§ 371 (c)(1),
(2), (4) Date: Feb. 14, 2011

(87) PCT Pub. No.: WO2009/142318
PCT Pub. Date: Nov. 26, 2009

(65) Prior Publication Data
US 2011/0160062 A1 Jun. 30, 2011

(30) Foreign Application Priority Data

May 20, 2008 (JP) .................... 2008-132190
Jan. 9, 2009 (JP) .................... 2009-003467

(51) Int. Cl.
*A01N 43/56* (2006.01)
*C07D 231/20* (2006.01)

(52) U.S. Cl.
USPC ............................. 504/282; 548/370.4

(58) Field of Classification Search
None
See application file for complete search history.

(56) References Cited

U.S. PATENT DOCUMENTS

| | | | |
|---|---|---|---|
| 4,942,246 A | 7/1990 | Tanaka et al. | |
| 4,948,887 A | 8/1990 | Baba et al. | |
| 4,986,845 A | 1/1991 | Oya et al. | |
| 8,119,569 B2 * | 2/2012 | Komyoji et al. | 504/282 |
| 2009/0286683 A1 | 11/2009 | Shimoharada et al. | |
| 2010/0075855 A1 | 3/2010 | Komyoji et al. | |
| 2010/0099563 A1 | 4/2010 | Shimoharada et al. | |
| 2010/0197500 A1 | 8/2010 | Kikugawa et al. | |
| 2010/0317528 A1 | 12/2010 | Shimoharada et al. | |

FOREIGN PATENT DOCUMENTS

| | | |
|---|---|---|
| CN | 88 1 01455 A | 9/1988 |
| CN | 1039586 A | 2/1990 |
| EP | 0 282 944 | 9/1988 |
| EP | 0 352 543 | 1/1990 |
| WO | 2007 069771 | 6/2007 |
| WO | 2008 065907 | 6/2008 |
| WO | WO 2008/078811 A1 | 7/2008 |
| WO | 2009 011321 | 1/2009 |

OTHER PUBLICATIONS

International Search Report issued Jul. 23, 2009 in PCT/JP09/59489 filed May 19, 2009.
Office Action issued Jun. 5, 2012, in Chinese Patent Application No. 200980118134.0 with English translation.
U.S. Appl. No. 13/133,993, filed Jun. 10, 2011, Kikugawa, et al.

* cited by examiner

*Primary Examiner* — Kamal Saeed
(74) *Attorney, Agent, or Firm* — Oblon, Spivak, McClelland, Maier & Neustadt, L.L.P.

(57) ABSTRACT

The present invention provides a novel herbicide showing excellent herbicidal effects, which has a wide application range including agricultural fields and non-agricultural fields and various application methods including soil treatment and foliage treatment. A pyrazole compound represented by the formula (I) or its salt: wherein $R^1$ is alkyl, $R^2$ is a hydrogen atom or alkyl, $R^3$ is alkyl, $R^4$ is alkyl, $R^5$ is alkyl substituted by one alkoxy, alkoxy substituted by one alkoxy, or alkoxycarbonyl, $R^6$ is alkylsulfonyl, A is alkylene substituted by at least one alkyl; a process for its production; a herbicide containing it as an active ingredient; and a method for controlling undesired plants or inhibiting their growth, which comprises applying a herbicidally effective amount thereof to the undesired plants or to a place where they grow.

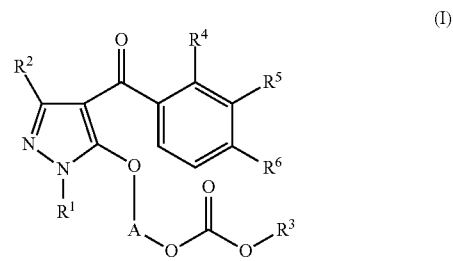

16 Claims, No Drawings

PYRAZOLE COMPOUNDS, PROCESS FOR THEIR PRODUCTION AND HERBICIDES CONTAINING THEM

TECHNICAL FIELD

The present invention relates to novel pyrazole compounds useful as an active ingredient of herbicides.

BACKGROUND ART

Patent Documents 1) and 2) disclose pyrazole compounds. However, pyrazole compounds represented by the following formula (I) or (II) are not specifically disclosed therein.
Patent Document 1): EP0352543A1
Patent Document 2): EP0282944A2

DISCLOSURE OF THE INVENTION

Object to be Accomplished by the Invention

Heretofore, herbicides which have excellent herbicidal activities against weeds and which are safe to crop plants, have been desired for labor saving in the operation of controlling weeds and for improvement of productivity of agricultural and horticultural plants. In development of new herbicides in future, it is desired to develop compounds capable of exhibiting desired herbicidal activities while their dosages are controlled to be low. Further, it is desired to develop compounds which will not adversely affect the environment by remaining in soil more than necessary while exhibiting practical residual effectiveness, or by flowing out of the active ingredient to soil outside of the applied site due to raining, etc. Further, it is desired to develop compounds which are highly safe to animals. However, search for novel compounds suitable for such an object depends on trial and error.

Means to Accomplish the Object

The present inventors have conducted extensive studies on pyrazole compounds in order to find more excellent herbicides which accomplish the above object and as a result, accomplished the present invention.

Namely, the present invention relates to a pyrazole compound represented by the formula (I) or its salt:

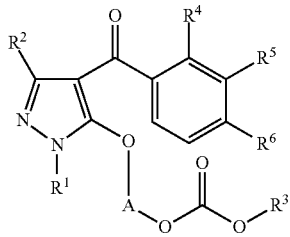

(I)

wherein $R^1$ is alkyl, $R^2$ is a hydrogen atom or alkyl, $R^3$ is alkyl, $R^4$ is alkyl, $R^5$ is alkyl substituted by one alkoxy, alkoxy substituted by one alkoxy, or alkoxycarbonyl, $R^6$ is alkylsulfonyl, A is alkylene substituted by at least one alkyl; a process for producing it; a herbicide containing it as an active ingredient; and a method for controlling undesired plants or inhibiting their growth, which comprises applying a herbicidally effective amount of it to the undesired plants or to a place where they grow.

Further, the present invention relates to a pyrazole compound represented by the formula (II) or its salt which is useful for intermediate of the pyrazole compound represented by the formula (I) or its salt, and also useful for herbicide:

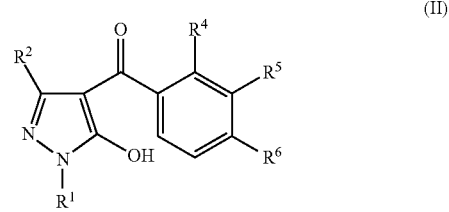

(II)

wherein $R^1$ is alkyl, $R^2$ is a hydrogen atom or alkyl, $R^4$ is alkyl, $R^5$ is alkyl substituted by one alkoxy, alkoxy substituted by one alkoxy, or alkoxycarbonyl, and $R^6$ is alkylsulfonyl; a process for producing it; a herbicide containing it as an active ingredient; and a method for controlling undesired plants or inhibiting their growth, which comprises applying a herbicidally effective amount of it to the undesired plants or to a place where they grow.

The pyrazole compounds represented by the formula (I) or (II), or their salts, realize a remarkable improvement in the herbicidal activities against weeds as compared with conventional compounds of similar types and have a high safety to crop plants. Further, they will not adversely affect the environment by remaining in soil more than necessary while exhibiting practical residual effectiveness, or by flowing out of the active ingredient to soil outside of the applied site due to raining, etc.

BEST MODE FOR CARRYING OUT THE INVENTION

In the above formula (I) or (II), the alkyl or alkyl moiety may be linear or branched, and specific examples thereof include $C_{1-9}$ alkyl such as methyl, ethyl, n-propyl, iso-propyl, n-butyl, iso-butyl, sec-butyl, tert-butyl, n-pentyl, iso-pentyl, neopentyl, tert-pentyl, n-hexyl, iso-hexyl, n-heptyl, n-octyl and n-nonyl.

In the above formula (I), the alkylene moiety may be a $C_{1-9}$ alkylene such as methylene, ethylene, trimethylene, tetramethylene, pentamethylene, hexamethylene, heptamethylene, octamethylene or nonamethylene.

The salt of the pyrazole compound represented by the above formula (I) or (II) includes all kinds of salts so long as they are agriculturally acceptable. Examples thereof include alkali metal salts such as a sodium salt and a potassium salt; alkaline earth metal salts such as a magnesium salt and a calcium salt; amine salts such as a dimethylamine salt and a triethylamine salt; inorganic acid salts such as a hydrochloride, a perchlorate, a sulfate and a nitrate; and organic acid salts such as an acetate and a methanesulfonate.

For the pyrazole compounds represented by the above formula (I) or (II), optical isomers may sometimes be present, and the present invention includes all of such isomers. In this specification, the compound is described as a mixture of isomers, unless otherwise specified.

The pyrazole compound represented by the above formula (I) or (II), or its salt (hereinafter referred to simply as the compound of the present invention) can be produced by the following reaction and in accordance with a usual method for producing a salt.

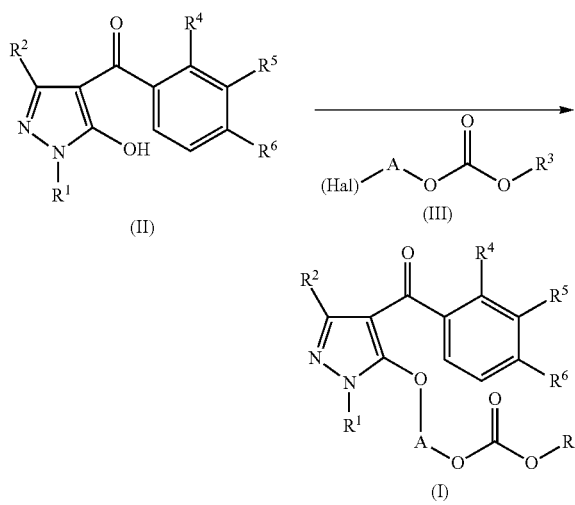

(A)

(I)

wherein $R^1$, $R^2$, $R^3$, $R^4$, $R^5$, $R^6$ and A are as defined above, and Hal is halogen.

The above reaction can be carried out in the presence of a solvent, as the case requires. The solvent may be any solvent so long as it is inert to the reaction. It may, for example, be a ketone such as acetone, ethyl methyl ketone or diethyl ketone; a halogenated hydrocarbon such as methylene chloride, chloroform, dichloroethane or trichloroethane; an aromatic hydrocarbon such as benzene, toluene, xylene, or nitrobenzene; an ester such as methyl acetate, ethyl acetate or propyl acetate; an aprotic polar solvent such as acetonitrile, N,N-dimethylformamide (DMF), dimethylsulfoxide (DMSO), dimethylacetamide (DMA), hexamethyl phosphoric acid triamide (HMPA) or sulfolane; or an ether such as diethyl ether, dioxane, tetrahydrofuran (THF) or dimethoxyethane. As the solvent, one or more of them may suitably be selected. Among such solvents, preferred are, for example, aromatic hydrocarbons.

The above reaction can be carried out in the presence of a base, as the case requires. The base may be either an inorganic base or an organic base. The organic base may, for example, be a tertiary amine such as triethylamine or diisopropylethylamine; pyridine, 4-(dimethylamino)pyridine, or 2,6-lutidine. The inorganic base may, for example, be an alkali metal carbonate such as sodium carbonate or potassium carbonate; an alkali metal hydrogencarbonate such as sodium hydrogencarbonate or potassium hydrogencarbonate; an alkaline earth metal carbonate such as calcium carbonate or barium carbonate; an alkali metal hydroxide such as sodium hydroxide or potassium hydroxide; or an alkali metal cyanide such as sodium cyanide or potassium cyanide. With respect to such bases, one or more of them may suitably be selected and mixed for use, in an amount of usually from 0.01 to 100, preferably from 0.1 to 10 equivalents to the compound of the formula (II).

The above reaction may be carried out in the presence of a catalyst. The catalyst may, for example, be n-butyl ammonium bromide, n-butyl ammonium chloride, tetra-n-butylphosphonium bromide, sodium iodide or potassium iodide. Among such catalysts, preferred is, for example, n-butylammonium bromide. One or more of such catalysts may suitably be selected or mixed for use in an amount of usually from 0.0001 to 10 equivalents, preferably from 0.001 to 1 equivalent.

The above reaction can be carried out at a reaction temperature of usually from 0° C. to 150° C., preferably from 50° C. to 120° C. for a reaction time of usually from 1 minute to 48 hours, preferably from 30 minutes to 5 hours.

As the compound of the formula (II) to be used in the above reaction, it is possible to use one obtained as a salt by the following reaction (B).

The pyrazole compound represented by the above formula (II) contains a novel compound, and may be produced in accordance with the following reaction (B).

(B)

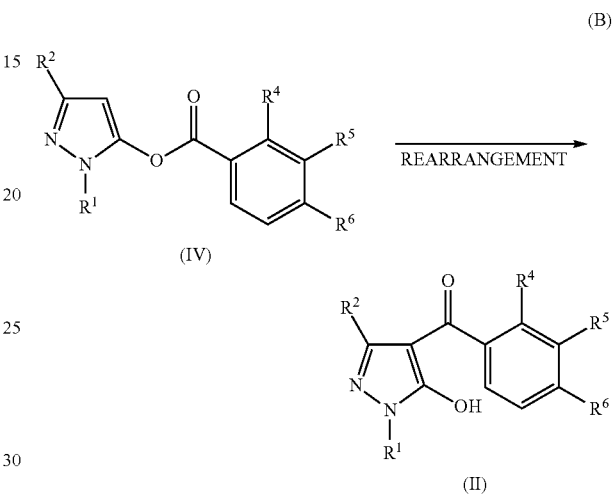

wherein $R^1$, $R^2$, $R^4$, $R^5$ and $R^6$ are as defined above.

Namely, the compound represented by the formula (II) can be produced by subjecting a compound represented by the formula (IV) to a rearrangement reaction.

The above reaction can be carried out in the presence of a solvent, as the case requires. The solvent may be any solvent so long as it is inert to the reaction. It may, for example, be a halogenated hydrocarbon such as methylene chloride, chloroform, dichloroethane or trichloroethane; an aromatic hydrocarbon such as benzene, toluene, xylene or nitrobenzene; an ester such as methyl acetate, ethyl acetate or propyl acetate; an aprotic polar solvent such as acetonitrile, DMF, DMSO, DMA, HMPA or sulfolane; or an ether such as diethyl ether, dioxane, THF or dimethoxyethane. As the solvent, one or more of them may suitably be selected. Among such solvents, preferred is, for example, an aromatic hydrocarbon or an aprotic polar solvent, and more preferred is, for example, an aromatic hydrocarbon to which an aprotic polar solvent is mixed. When an aprotic polar solvent is mixed to an aromatic hydrocarbon, its mixing ratio is, for example, usually from 1 to 20 parts by volume, preferably from 5 to 10 parts by volume, per 100 parts by volume of the aromatic hydrocarbon.

The above reaction can be carried out in the presence of a base, as the case requires. The base may be either an organic base or an inorganic base, and those exemplified in the above reaction (A) may, for example, be mentioned. With respect to these bases, one or more of them may suitably be selected or mixed for use in an amount of usually from 0.01 to 100, preferably from 0.1 to 10 equivalents to the compound of the formula (IV). Among such bases, preferred is, for example, an alkali metal carbonate. When a base is used, the compound of the formula (II) may sometimes be obtained in the state of a salt. Even when the compound of the formula (II) is in the state of a salt, such a salt of the compound of the formula (II) may be used as it is as a material for the above reaction (A).

Further, in the above reaction, a catalyst may be added as the case requires. As such a catalyst, acetone cyanohydrin may be used from 0.01 to 10 equivalents to the compound of the formula (IV).

The above reaction can be carried out at a reaction temperature of usually from 0° C. to 150° C., preferably from 70° C. to 150° C. for a reaction time of usually from 1 minute to 48 hours, preferably from 30 minutes to 5 hours.

The compound represented by the above formula (IV) may be prepared in accordance with the following reaction (C).

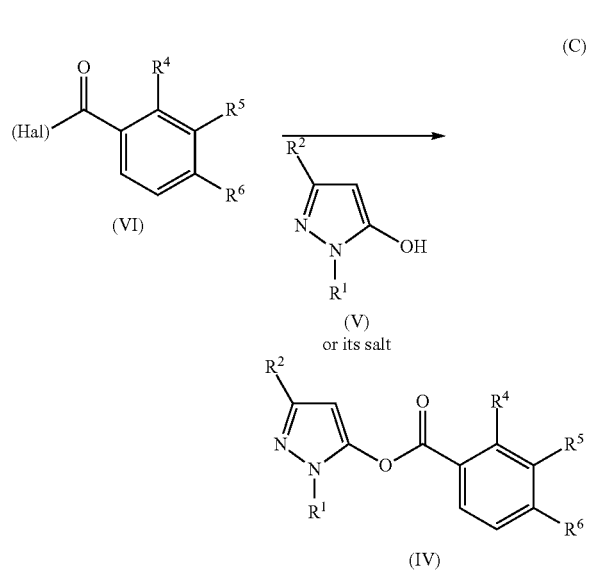

wherein $R^1$, $R^2$, $R^4$, $R^5$, $R^6$ and Hal are as defined above.

Namely, the compound represented by the formula (IV) can be produced by reacting a compound represented by the formula (V) or its salt, such as a hydrochloride, a sulfate or a nitrate, with a compound represented by the formula (VI). The compound of the formula (V) or its salt may be used in an amount of from 0.01 to 100, preferably from 0.1 to 10 equivalents to the compound of the formula (VI).

The above reaction can be carried out in the presence of a solvent, as the case requires. The solvent may be any solvent so long as it is inert to the reaction, and those exemplified in the above reaction (B) may, for example, be mentioned. One or more of them may suitably be selected. Among such solvents, preferred is, for example, an aromatic hydrocarbon.

The above reaction can be carried out in the presence of a base, as the case requires. The base may be an organic base or an inorganic base, and those exemplified in the above reaction (A) may, for example, be mentioned. With respect to such bases, one or more of them may suitably be selected and mixed for use in an amount of usually from 0.005 to 50, preferably from 0.05 to 5 equivalents to the compound of the formula (VI). Among such bases, preferred is, for example, a tertiary amine.

The reaction temperature for the above reaction is usually from 0° C. to 150° C., preferably from 10° C. to 100° C., and the reaction time is usually from 1 minute to 48 hours, preferably from 30 minutes to 5 hours.

The compound represented by the above formula (VI) can be produced in accordance with the following reaction (D).

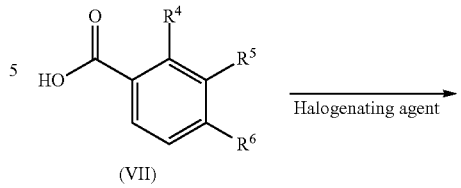

wherein $R^4$, $R^5$, $R^6$ and Hal are as defined above.

In the above reaction, a halogenating agent such as thionyl chloride or oxalyl chloride is reacted in an amount of usually from 0.01 to 100, preferably from 0.1 to 10 equivalents to the compound represented by the formula (VII). Among such halogenating agents, preferred is, for example, thionyl chloride.

The above reaction can be carried out in the presence of a solvent, as the case requires. The solvent may be any solvent so long as it is a solvent inert to the reaction, and those exemplified in the above reaction (B) may, for example, be mentioned. One or more of them may suitably be selected. Among such solvents, preferred is, for example, an aromatic hydrocarbon or a halogenated hydrocarbon, and more preferred is, for example, an aromatic hydrocarbon.

For the above reaction, a catalyst may be used as the case requires. The catalyst may, for example, be DMF. The catalyst may be used in an amount of usually from 0.001 to 1, preferably from 0.01 to 0.5 equivalent to the compound represented by the formula (VII).

The reaction temperature for the above reaction is usually from 0° C. to 150° C., preferably from 10° C. to 120° C. and the reaction time is usually from 1 minute to 48 hours, preferably from 30 minutes to 5 hours.

The compound represented by the above formula (IV) can be produced in accordance with the following reaction (E), other than the above-mentioned methods.

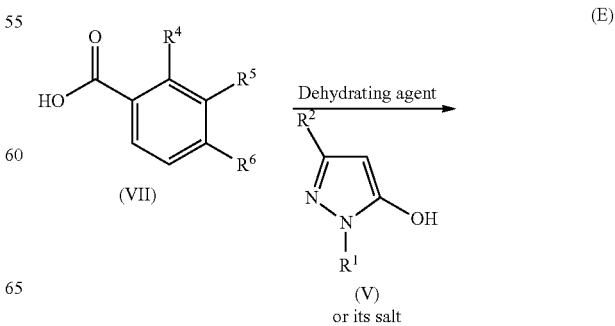

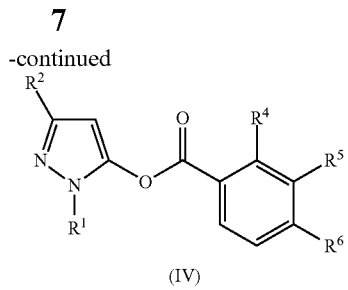

(IV)

wherein $R^1$, $R^2$, $R^4$, $R^5$ and $R^6$ are as defined above.

Namely, the compound represented by the formula (IV) can be produced by reacting a compound represented by the formula (V) or its salt, such as a hydrochloride, a sulfate or a nitrate, with a compound represented by the formula (VII) by means of a dehydrating agent.

The dehydrating agent to be used for the above reaction may, for example, be DCC (dicyclohexylcarbodiimide) or 1-ethyl-3-(3-dimethylaminopropyl)-carbodiimide hydrochloride.

The above reaction can be carried out in the presence of a solvent, as the case requires. The solvent may be any solvent so long as it is inert to the reaction, and those exemplified in the above reaction (B) may, for example, be mentioned. One or more of them may suitably be selected.

The above reaction can be carried out in the presence of a base, as the case requires. The base may, for example, be a tertiary amine such as triethylamine and diisopropylethylamine; pyridine, 4-(dimethylamino)pyridine or 2,6-lutidine. As the base, one or more of them may suitably be selected and mixed for use in an amount of from 1 to 100 equivalents to the compound represented by the formula (VII).

The above reaction can be carried out at a reaction temperature of usually from 0° C. to 150° C. for a reaction time of usually from 1 minute to 48 hours.

The compound represented by the above formula (VII) can be produced in accordance with the following reaction (F).

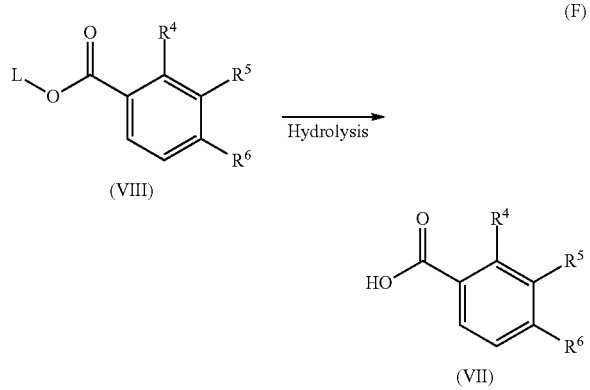

wherein $R^4$, $R^5$ and $R^6$ are as defined above, and L is a protective group such as alkyl.

The compound represented by the formula (VII) can be produced by subjecting a compound represented by the formula (VIII) to hydrolysis in the presence of water.

The above reaction can be carried out in the presence of a solvent, as the case requires. The solvent may be any solvent so long as it is inert to the reaction, and it may, for example, be an aromatic hydrocarbon such as benzene, toluene or xylene; an aprotic polar solvent such as acetonitrile, DMF, DMSO, DMA, HMPA or sulfolane; an ether such as diethyl ether, dioxane, THF or dimethoxyethane; an alcohol such as methanol or ethanol; or water. As the solvent, one or more of them may suitably be selected.

The above reaction can be carried out in the presence of a base or an acid, as the case requires. The base may be either an organic base or an inorganic base, and those exemplified in the above reaction (A) may, for example, be mentioned. The acid may, for example, be hydrochloric acid, sulfuric acid or perchloric acid. As the base or acid, one or more of them may suitably be selected and mixed for use in an amount of from 1 to 100 equivalents to the compound represented by the formula (VIII).

The above reaction can be carried out at a reaction temperature of usually from 0° C. to 150° C. for a reaction time of usually from 1 minute to 48 hours.

Among the compounds represented by the above formula (VIII), a compound wherein $R^5$ is $R^{5-a-1}$ can be produced in accordance with the following reaction (G).

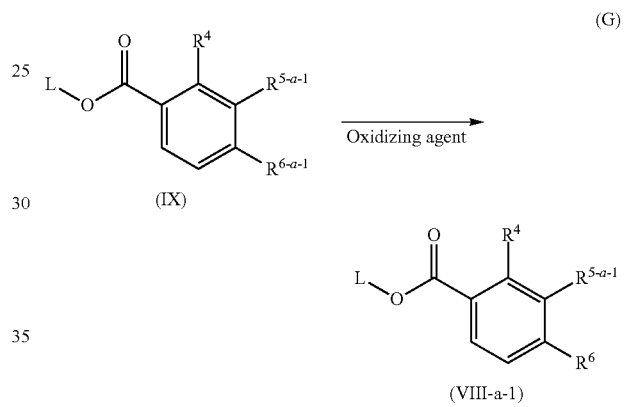

wherein $R^{5-a-1}$ is alkoxy substituted by one alkoxy, $R^{6-a-1}$ is alkylthio, and L, $R^4$ and $R^6$ are as defined above.

Namely, the compound represented by the formula (VIII-a-1) can be produced by reacting a compound represented by the formula (IX) with an oxidizing agent in the presence of a solvent.

The oxidizing agent to be used in the above reaction may, for example, be hydrogen peroxide, peracetic acid or methachloroperbenzoic acid.

The solvent to be used for the above reaction may be any solvent so long as it is inert to the reaction, and it may, for example, be a halogenated hydrocarbon such as methylene chloride, chloroform, dichloroethane or trichloroethane; a ketone such as acetone or methyl ethyl ketone; an ether such as diethyl ether, dioxane, THF or dimethoxyethane; or acetic acid. As the solvent, one or more of them may suitably be selected.

The above reaction can be carried out at a reaction temperature of usually from 0° C. to 150° C. for a reaction time of usually from 1 minute to 48 hours.

The above reaction can be carried out in the presence of a catalyst, as the case requires. The catalyst may, for example, be sodium tungstate or its hydrate.

The compound represented by the above formula (IX) can be produced in accordance with the following reaction (H).

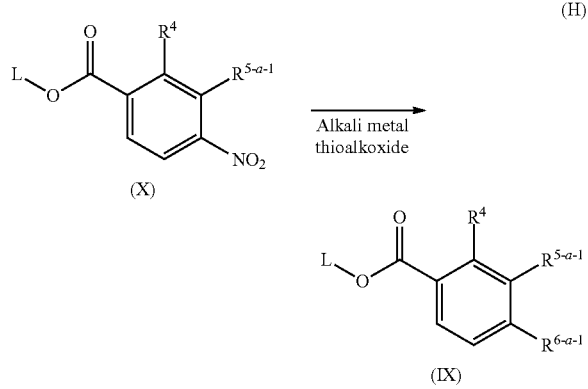

wherein L, $R^4$, $R^{5-a-1}$ and $R^{6-a-1}$ are as defined above.

Namely, the compound represented by the formula (IX) can be produced by reacting a compound represented by the formula (X) with an alkali metal thioalkoxide.

The alkali metal thioalkoxide to be used for the above reaction may, for example, be sodium thiomethoxide or sodium thioethoxide.

The above reaction can be carried out in the presence of a solvent, as the case requires. The solvent may be any solvent so long as it is inert to the reaction, and it may, for example, be an aprotic polar solvent such as acetonitrile, DMF, DMSO, DMA, HMPA, sulfolane or dimethoxyethane. As the solvent, one or more of them may suitably be selected.

The above reaction can be carried out at a reaction temperature of usually from 0° C. to 150° C. for a reaction time of usually from 1 minute to 48 hours.

The compound represented by the above formula (X) can be produced in accordance with the following reaction (I).

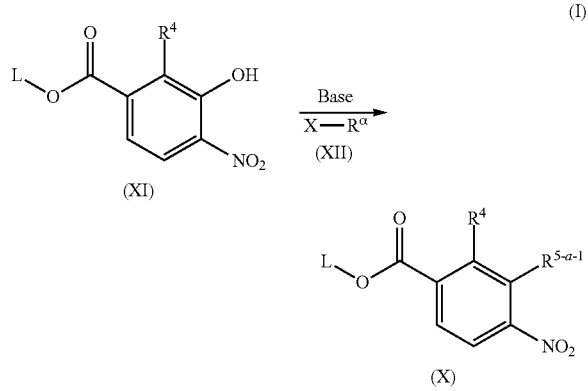

wherein $R^\alpha$ is alkyl substituted by one alkoxy, X is a leaving group such as halogen or a methane sulfonyloxy group, and L, $R^4$ and $R^{5-a-1}$ are as defined above.

Namely, the compound represented by the formula (X) can be produced by reacting a compound represented by the formula (XI) with a compound represented by the formula (XII) in the presence of a base.

The base to be used in the above reaction may be either an inorganic base or an organic base. The organic base may, for example, be triethylamine, diisopropylethylamine, pyridine, 4-(dimethylamino)pyridine or 2,6-lutidine. The inorganic base may, for example, be an alkali metal carbonate such as sodium carbonate or potassium carbonate; an alkali metal hydroxide such as sodium hydroxide or potassium hydroxide; or an alkali metal hydride such as sodium hydride or potassium hydride. As the base, one or more of them may suitably be selected and mixed for use in an amount of from 0.5 to 100 equivalents to the compound represented by the formula (XI).

The above reaction can be carried out in the presence of a solvent, as the case requires. The solvent may be any solvent so long as it is inert to the reaction, and those exemplified in the above reaction (B) may, for example be mentioned. One or more of them may suitably be selected.

The above reaction can be carried out in the presence of a catalyst, as the case requires. The catalyst may, for example, be potassium iodide or tetra-n-butylammonium iodide.

The above reaction can be carried out at a reaction temperature of usually from 0° C. to 150° C. for a reaction time of usually from 1 minute to 48 hours.

The compound represented by the above formula (VIII-a-1) can be produced in accordance with the following reaction (J), other than the above method.

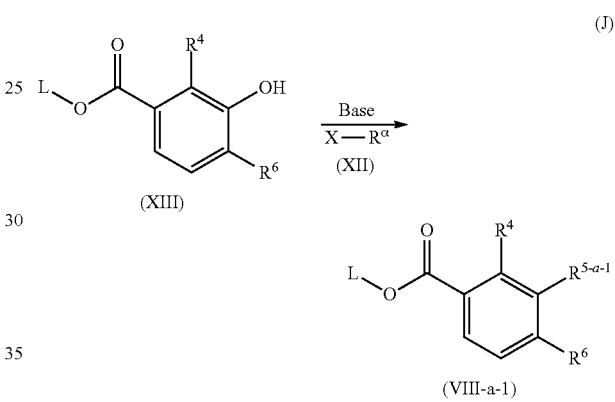

wherein L, $R^4$, $R^{5-a-1}$, $R^6$, $R^\alpha$ and X are as defined above.

Namely, the compound represented by the formula (VIII-a-1) can be produced by reacting a compound represented by the formula (XIII) with a compound represented by the formula (XII) in the presence of a base.

The above reaction can be carried out in the same manner as the above reaction (I).

The compound represented by the above formula (XIII) can be produced in accordance with the following reaction (K).

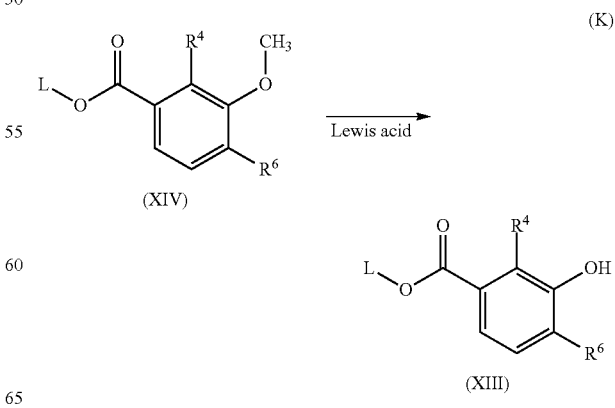

wherein $R^4$, $R^6$ and L are as defined above.

Namely, the compound represented by the formula (XIII) can be produced by reacting a compound represented by the formula (XIV) with a Lewis acid such as boron tribromide, aluminum chloride or iron bromide.

The above reaction can be carried out in the presence of a solvent, as the case requires. The solvent may be any solvent so long as it is inert to the reaction, and it may, for example, be a halogenated hydrocarbon such as methylene chloride, chloroform, dichloroethane or trichloroethane; an aromatic hydrocarbon such as benzene, toluene or xylene; or an ester such as methyl acetate, ethyl acetate or propyl acetate. As the solvent, one or more of them may be suitably selected.

The above reaction can be carried out at a reaction temperature of usually from 0° C. to 150° C. for a reaction time of usually from 1 minute to 48 hours.

The compound represented by the above formula (XIV) can be produced in accordance with the following reaction (L).

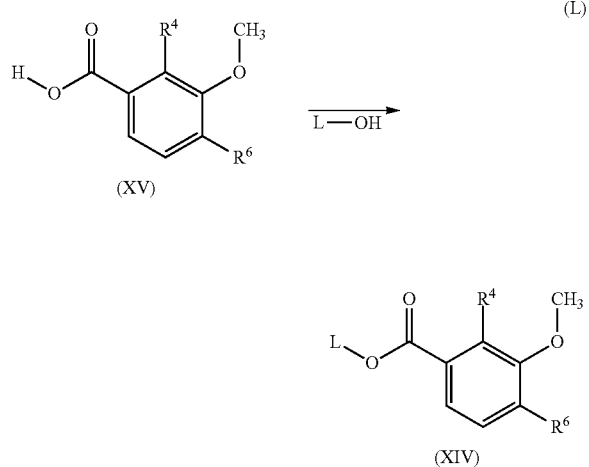

wherein $R^4$, $R^6$ and L are as defined above.

Namely, the compound represented by the formula (XIV) can be produced by a reaction of introducing a protective group L into a compound represented by the formula (XV).

The above reaction can be carried out in the presence of a solvent, as the case requires. The solvent may be any solvent so long as it is inert to the reaction, and it may, for example, be an aromatic hydrocarbon such as benzene, toluene or xylene; an ester such as methyl acetate, ethyl acetate or propyl acetate; a halogenated hydrocarbon such as methylene chloride, chloroform, dichloroethane or trichloroethane; or an aprotic polar solvent such as acetonitrile, DMF, DMSO, DMA, HMPA or sulfolane. As the solvent, one or more of them may be suitably selected.

The above reaction can be carried out in the presence of an acid, as the case requires. The acid to be used for the above reaction may, for example, be hydrochloric acid or sulfuric acid.

The above reaction can be carried out at a reaction temperature of usually from 0° C. to 150° C. for a reaction time of usually from 1 minute to 48 hours.

Among the compounds represented by the above formula (VIII), a compound wherein $R^5$ is $R^{5-a-2}$ can be produced in accordance with the following reaction (M).

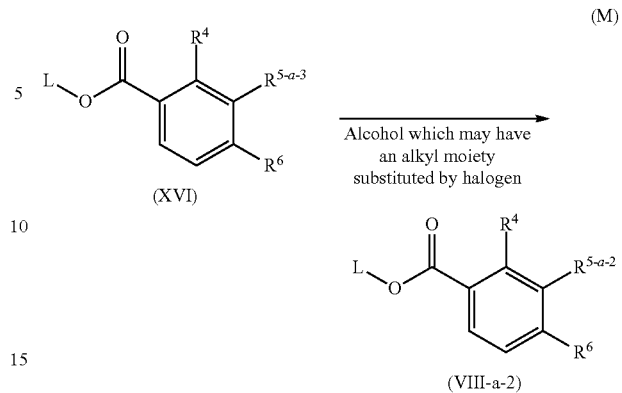

wherein $R^{5-a-2}$ is alkyl substituted by one alkoxy, $R^{5-a-3}$ is bromoalkyl, and L, $R^4$ and $R^6$ are as defined above.

The above reaction can be carried out in the presence of a solvent, as the case requires. The solvent may be any solvent so long as it is inert to the reaction, and it may, for example, be an alcohol such as methanol or ethanol; an ester such as methyl acetate, ethyl acetate or propyl acetate; an ether such as diethyl ether, dioxane, THF or dimethoxyethane; or an aprotic polar solvent such as acetonitrile, DMF, DMSO, DMA, HMPA or sulfolane. As the solvent, one or more of them may suitably be selected.

The above reaction can be carried out in the presence of a base, as the case requires. The base may, for example, be an alkali metal hydride such as sodium hydride or potassium hydride.

The above reaction can be carried out at a reaction temperature of usually from 0° C. to 150° C. for a reaction time of usually from 1 minute to 48 hours.

The compound represented by the above formula (VII) can be produced in accordance with the following reaction (N).

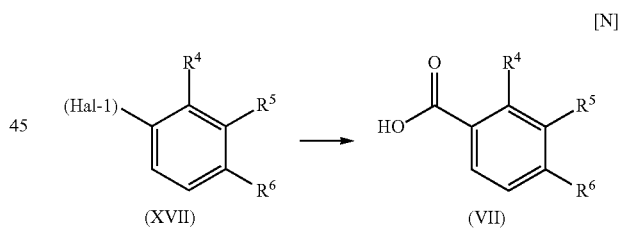

wherein $R^4$, $R^5$ and $R^6$ are as defined above, and Hal-1 is halogen.

Namely, the compound represented by the formula (VII) can be produced by reacting the compound represented by the formula (XVII), carbon monoxide or its equivalent, and $H_2O$, in the presence of a catalyst and a base.

The base to be used in the above reaction may be an inorganic base or an organic base. The organic base may, for example, be triethylamine, tributylamine, diisobutyl ethylamine, pyridine, 4-(dimethylamino)pyridine or 2,6-lutidine. The inorganic base may, for example, be an alkali metal carbonate such as sodium carbonate, potassium carbonate or cesium carbonate; an alkali metal hydroxide such as sodium hydroxide or potassium hydroxide; an alkaline earth metal hydroxide such as calcium hydroxide or barium hydroxide; or an alkali metal acetate such as sodium acetate or potassium acetate. One or more of such bases may suitably be selected or mixed for use in an amount of usually from 0.1 to 100 equivalents, preferably from 0.5 to 10 equivalents, to the compound represented by the formula (XVII). Among these bases, preferred may be an alkali metal carbonate.

The catalyst to be used in the above reaction may, for example, be a metallic catalyst, for example, a palladium catalyst such as palladium chloride, palladium acetate, tetrakis(triphenylphosphine)palladium, dichlorobis(triphenylphosphine)palladium, trans-di(μ-acetate)bis[o-(di-o-tolylphosphino)benzyl]dipalladium or palladium carbon; a ruthenium catalyst such as triruthenium dodecacarbonyl; or a rhodium catalyst such as chlorobis(cyclooctene)rhodium (I). One or more of such catalysts may suitably be selected or mixed for use in an amount of usually from $10^{-10}$ to 1 equivalent, preferably from $10^{-5}$ to 0.1 equivalent, to the compound represented by the formula (XVII). Among these catalysts, preferred may be a palladium catalyst.

The equivalent to carbon monoxide to be used in the above reaction may, for example, be hexacarbonyl molybdenum, formic acid or chloroform. The carbon monoxide or its equivalent may be reacted in an amount of from 1 to 1,000 equivalents to the compound represented by the formula (XVII), if necessary, under elevated pressure. The pressure may be suitably selected within a range of from 1 to 100 MPa, preferably from 1 to 10 MPa.

The above reaction may be carried out in the presence of a solvent, as the case requires. The solvent may be any solvent so long as it is inert to the reaction, and it may, for example, be an alcohol such as methanol, ethanol, n-propanol, i-propanol, n-butyl alcohol, i-butyl alcohol, sec-butyl alcohol or t-butyl alcohol; water; a halogenated hydrocarbon such as methylene chloride, chloroform, dichloroethane or trichloroethane; an aromatic hydrocarbon such as benzene, toluene, xylene, nitrobenzene or chlorobenzene; an ester such as methyl acetate, ethyl acetate or propyl acetate; an aprotic polar solvent such as acetonitrile, DMF, DMSO, DMA, HMPA or sulfolane; or an ether such as diethyl ether, 1,4-dioxane, THF or 1,2-dimethoxyethane. As the solvent, one or more of such solvents may suitably be selected for use. Among these solvents, preferred may, for example, be an alcohol, and further preferred may, for example, be a $C_4$ alcohol.

The above reaction may be carried out in the presence of a ligand, as the case requires. The ligand may, for example, be tri-t-butylphosphine, tricyclohexylphosphine, triphenylphosphine, trio-tolyl)phosphine, 1,4-bis(diphenylphosphino)butane, 1,3-bis(diphenylphosphino)pentane or 1,1'-bis(diphenylphosphino)ferrocene. One or more of such ligands may suitably be selected or mixed for use in an amount of from $10^{-10}$ to 1 equivalent, preferably from $10^{-5}$ to 1 equivalent, to the compound represented by the formula (XVII).

The above reaction may be carried out in the presence of a cocatalyst, as the case requires. The cocatalyst may, for example, be an alkali metal halide such as sodium chloride, potassium chloride, sodium bromide or potassium bromide; or a quaternary ammonium salt such as tetra(n-butyl)ammonium bromide. One or more of such cocatalysts may suitably be selected or mixed for use in an amount of usually from 0.001 to 1 equivalent, preferably from 0.01 to 0.1 equivalent, to the compound represented by the formula (XVII).

The above reaction may be carried out in the presence of an inert gas as the case requires. The inert gas may, for example, be a nitrogen gas or an argon gas.

The reaction temperature for the above reaction is usually from 0° C. to 300° C., preferably from 120° C. to 180° C., and the reaction time is usually from 1 minute to 72 hours, preferably from 1 hour to 24 hours.

Among compounds represented by the above formula (XVII), a compound wherein $R^5$ is $R^{5-a-1}$ can be produced in accordance with the following reaction (O):

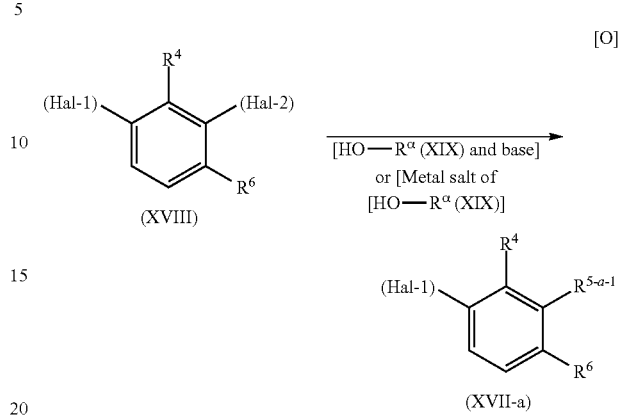

wherein $R^\alpha$, Hal-1, $R^{5-a-1}$, $R^4$ and $R^6$ are as defined above, and Hal-2 is halogen, provided that Hal-1 and Hal-2 may be the same or different from each other.

The above reaction can be carried out in the presence of a base as the case requires. The base may, for example, be an alkali metal carbonate such as sodium carbonate, potassium carbonate or cesium carbonate; an alkaline earth metal carbonate such as calcium carbonate or barium carbonate; an alkali metal hydroxide such as lithium hydroxide, sodium hydroxide or potassium hydroxide; an alkaline earth metal hydroxide such as calcium hydroxide or barium hydroxide; an alkali metal hydride such as lithium hydride, sodium hydride or potassium hydride; an alkali lithium reagent such as n-butyl lithium; sodium amide ($NaNH_2$); or a Grignard reagent such as methylmagnesium bromide or isopropylmagnesium chloride. Among these bases, preferred may, for example, be an alkali metal hydroxide or an alkali metal carbonate, and more preferred may, for example, be an alkali metal hydroxide. These bases may be used in an amount of usually from 0.02 to 200 equivalents, preferably from 0.2 to 20 equivalents, to the compound represented by the formula (XVIII). Further, one or more of these bases may suitably be selected or mixed for use.

The metal salt of the compound represented by the formula (XIX) which may be used in the above reaction, may, for example, be an alkali metal salt such as a sodium salt or a potassium salt. The compound of the formula (XIX) or its metal salt may be employed within a range of usually from 0.01 to 100 equivalents, preferably from 0.1 to 10 equivalents, to the compound of the formula (XVIII).

The above reaction may be carried out in the presence of a solvent as the case requires. The solvent may be any solvent so long as it is inert to the reaction, and it may, for example, be an alcohol such as methanol, ethanol or 2-methoxyethanol; an ether such as diethyl ether, tetrahydrofuran, 1,4-dioxane, 1,2-dimethoxyethane or cyclohexyl methyl ether; an aprotic polar solvent such as DMF, DMSO, DMA or sulfolane; or a nonpolar solvent, such as a halogenated hydrocarbon such as methylene chloride, chloroform, dichloroethane or trichloroethane, or an aromatic hydrocarbon such as benzene, toluene, xylene, nitrobenzene or chlorobenzene. Further, the compound represented by the formula (XIX) may serve as a reaction reagent and as a solvent at the same time. As the solvent, one or more of them may suitably be selected.

Among these solvents, preferred may, for example, be a nonpolar solvent, and more preferred may, for example, be an aromatic hydrocarbon.

The above reaction may be carried out in an inert gas, as the case requires. The inert gas may, for example, be nitrogen gas or argon gas.

The reaction temperature in the above reaction is usually from 0° C. to 200° C., preferably from 70° C. to 150° C., and the reaction time is usually from 1 minute to 48 hours, preferably from 30 minutes to 10 hours.

The compound represented by the above formula (XVIII) can be produced in accordance with the following reaction (P).

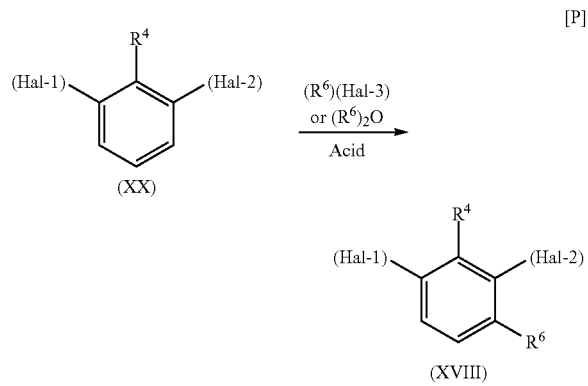

wherein $R^4$, $R^6$, Hal-1 and Hal-2 are as defined above, Hal-3 is halogen, and Hal-1, Hal-2 and Hal-3 may be the same or different from one another.

The acid to be used in the above reaction may, for example, be a Lewis acid such as zinc chloride, zinc bromide, aluminum chloride, aluminum bromide, iron chloride, bismuth chloride, indium chloride, antimony chloride, boron tribromide or iron bromide; methanesulfonic acid, sulfuric acid or trifluoromethanesulfonic acid, and it can be used within a range of usually from 0.01 to 100 equivalents, preferably from 0.1 to 10 equivalents, to the compound represented by the formula (XX). One or more of such acids may suitably be selected for use. Among these acids, preferred may, for example, be iron chloride.

The alkylsulfonyl halide [$(R^6)$(Hal-3)] or the alkylsulfonic acid anhydride [$(R^6)_2O$] to be used in the above reaction may be used within a range of usually from 0.01 to 100 equivalents, preferably from 0.1 to 10 equivalents, to the compound represented by the formula (XX). The halogen in the alkylsulfonyl halide may, for example, be fluorine, chlorine, bromine or iodine. Among such an alkylsulfonyl halide or alkylsulfonic acid anhydride, preferred may, for example, be an alkylsulfonyl halide.

The above reaction may be carried out in the presence of a solvent, as the case requires. The solvent may be any solvent so long as it is inert to the reaction, and it may, for example, be a halogenated hydrocarbon such as methylene chloride, chloroform, dichloroethane or trichloroethane; carbon disulfide or nitromethane. One or more of such solvents may suitably be selected for use. Further, the compound represented by the formula (XX) may serve as the reaction reagent and the solvent at the same time.

The reaction temperature for the above reaction is usually from 0° C. to 250° C., preferably from 100° C. to 150° C., and the reaction time is usually from 1 minute to 48 hours, preferably from 30 minutes to 12 hours.

When the reaction mixture containing the compound of the formula (XVIII) and the acid, obtained after the above reaction, is left to cool, an inorganic acid and an alcohol solvent are gradually added, whereby even after completion of the cooling, the reaction mixture will not be solidified, such being advantageous from the viewpoint of the handling efficiency, and it tends to be easy to obtain a product of the compound of the formula (XVIII) with little impurities. The inorganic acid to be used here may, for example, be hydrochloric acid, sulfuric acid, nitric acid or a mixture thereof, and preferred may, for example, be hydrochloric acid. Further, the alcohol solvent may, for example, be methanol, ethanol, n-propanol, i-propanol, n-butanol, sec-butanol, i-propanol or tert-butanol, and preferred may, for example, be a $C_3$ alcohol such as n-propanol or i-propanol. The order of addition of the inorganic acid and the alcohol solvent may be such that either one is added first, or both may be added simultaneously. However, it is preferred that the inorganic acid is gradually added and then the alcohol solvent is added, so that the temperature of the reaction mixture will not rapidly decrease and be solidified by the addition.

The compounds of the present invention have excellent herbicidal effects when used as an active ingredient of herbicides. The application range extends to agricultural fields such as paddy fields, crop plant fields, orchards and mulberry fields and non-agricultural fields such as forest land, farm roads, play grounds and factory sites. The application method may suitably be selected from soil application, foliar application, water application, etc.

The compounds of the present invention are capable of controlling a wide range of undesired weeds, such as gramineae such as barnyardgrass (*Echinochloa crus-galli* L., *Echinochloa oryzicola* vasing.), crabgrass (*Digitaria sanquinalis* L., *Digitaria ischaemum* Muhl., *Digitaria adscendens* Henr., *Digitaria microbachne* Henr., *Digitaria horizontalis* Willd.), green foxtail (*Setaria viridis* L.), giant foxtail is (*Setaria faberi* Herrm.), yellow foxtail (*Setaria lutescens* Hubb.), goosegrass (*Eleusine indica* L.), wild oat (*Avena fatua* L.), johnsongrass (*Sorghum halepense* L.), quackgrass (*Agropyron repens* L.), alexandergrass (*Brachiaria plantaginea*), guineagrass (*Panicum maximum* Jacq.), paragrass (*Panicum purpurascens*), sprangletop (*Leptochloa chinensis*), red sprangletop (*Leptochloa panicea*), annual bluegrass (*Poa annua* L.), black grass (*Alopecurus myosuroides* Huds.), cholorado bluestem (*Agropyron tsukushiense* (Honda) Ohwi), broadleaf signalgrass (*Brachiaria platyphylla* Nash), southern sandbur (*Cenchrus echinatus* L.), italian ryegrass (*Lolium multiflorum* Lam.), and bermudagrass (*Cynodon dactylon* Pers.); cyperaceae such as rice flatsedge (*Cyperus iria* L.), purple nutsedge (*Cyperus rotundus* L.), yellow nutsedge (*Cyperus esculentus* L.), Japanese bulrush (*Scirpus juncoides*), flatsedge (*Cyperus serotinus*), small-flower umbrellaplant (*Cyperus difformis*), slender spikerush (*Eleocharis acicularis*), and water chestnut (*Eleocharis kuroguwai*); alismataceae such as Japanese ribbon waparo (*Sagittaria pygmaea*), arrow-head (*Sagittaria trifolia*), and narrowleaf waterplantain (*Alisma canaliculatum*); pontederiaceae such as monochoria (*Monochoria vaginalis*), and monochoria species (*Monochoria korsakowii*); scrophulariaceae such as false pimpernel (*Lindemia pyxidaria*), and abunome (*Dopatrium junceum*); lythraceae such as toothcup (*Rotala india*), and red stem (*Ammannia multiflora*); elatinaceae such as long stem waterwort (*Elatine triandra* SCHK.); malvaceae such as velvetleaf (*Abutilon theophrasti* MEDIC.), and prickly sida (*Sida spinosa* L.); compositae such as common cocklebur (*Xanthium strumarium* L.), common ragweed (*Ambrosia elatior* L.), thistle (*Breea setosa*

(BIEB.) KITAM.), hairy galinsoga (*Galinsoga ciliata* Blake), wild chamomile (*Matricaria chamomilla* L.); solanaceae such as black nightshade (*Solanum niarum* L.), and jimsonweed (*Datura stramonium*); amaranthaceae such as slender amaranth (*Amaranthus viridis* L.), and redroot pigweed (*Amaranthus retroflexus* L.); polygonaceeae such as pale smartweed (*Polygonum lapathifolium* L.), ladysthumb (*Polygonum persicaria* L.), wild buckwheat (*Polygonum convolvulus* L.), and knotweed (*Polygonum aviculare* L.); cruciferae such as flexuous bittercress (*Cardamine flexuosa* WITH.), shepherd's-purse (*Capsella bursa-pastoris* Medik.), and indian mustard (*Brassica juncea* Czern.); convolvulaceae such as tall momingglory (*Ipomoea purpurea* L.), field bindweed (*Calystegia arvensis* L.), and ivyleaf morningglory (*Ipomoea hederacea* Jacq.); Chenopodiaceae such as common lambsquarters (*Chenopodium album* L.), and mexican burningbush (*Kochia scoparia* Schrad.); Portulacaceae such as common purslane (*Portulaca oleracea* L.); leguminosae such as sicklepod (*Cassia obtusifolia* L.); caryophyllaceae such as common chickweed (*Stellaria media* L.); labiatae such as henbit (*Lamium amplexicaule* L.); rubiaceae such as catchweed (*Galium spurium* L.); euphorbiaceae such as threeseeded copperleaf (*Acalvpha australis* L.); and Commelinaceae such as common dayflower (*Commelina communis* L.).

Therefore, they can be effectively used for selectively controlling noxious weeds or nonselectively controlling noxious weeds in cultivation of useful crops such as corn (*Zea mays* L.), soybean (*Glycine max* Merr.), cotton (*Gossypium* spp.), wheat (*Triticum* spp.), rice (*Oryza sativa* L.), barley (*Hordeum vulgare* L.), rye (*Secale cereale* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), japanese lawngrass (*Zoysia japonica stend*), peanut (*Arachis hypogaea* L.), flax (*Linum usitatissimum* L.), tobacco (*Nicotiana tabacum* L.), and coffee (*Coffea* spp.). Particularly, the compounds of the present invention are effectively used for selectively controlling noxious weeds in cultivation of corn, soybean, cotton, wheat, rice, rape, sunflower, sugar beet, sugar cane, japanese lawngrass, peanut, flax, tobacco, coffee, and the like, and among these, especially corn, wheat, rice, japanese lawngrass and the like. In cultivation of such crop plants, for example, in cultivation of corn, among the above-mentioned noxious weeds, gramineae and malvaceae are, for example, typical noxious weeds, and green foxtail, guineagrass and velvet leaf belonging thereto may, for example, be mentioned as hardly controllable weeds. While having safety to crop plants, the compounds of the present invention can be used particularly is effectively not only to control the above noxious weeds but also to control hardly controllable noxious weeds such as green foxtail, guineagrass, velvet leaf and giant foxtail.

The compound of the present invention may be mixed with various agricultural additives and applied in the form of various formulations such as dusts, granules, water dispersible granules, wettable powders, tablets, pills, capsules (including a formulation packaged by a water soluble film), water-based suspensions, oil-based suspensions, microemulsions, suspoemulsions, water soluble powders, emulsifiable concentrates, soluble concentrates or pastes. It may be formed into any formulation which is commonly used in this field, so long as the object of the present invention is thereby met.

The additives to be used for the formulation include, for example, a solid carrier such as diatomaceous earth, slaked lime, calcium carbonate, talc, white carbon, kaoline, bentonite, a mixture of kaolinite and sericite, clay, sodium carbonate, sodium bicarbonate, mirabilite, zeolite or starch; a solvent such as water, toluene, xylene, solvent naphtha, dioxane, acetone, isophorone, methyl isobutyl ketone, chlorobenzene, cyclohexane, dimethyl sulfoxide, N,N-dimethylformamide, dimethylacetamide, N-methyl-2-pyrrolidone or an alcohol; an anionic surfactant such as a salt of fatty acid, a benzoate, an alkylsulfosuccinate, a dialkylsulfosuccinate, a polycarboxylate, a salt of alkylsulfuric acid ester, an alkyl sulfate, an alkylaryl sulfate, an alkyl diglycol ether sulfate, a salt of alcohol sulfuric acid ester, an alkyl sulfonate, an alkylaryl sulfonate, an aryl sulfonate, a lignin sulfonate, an alkyldiphenyl ether disulfonate, a polystyrene sulfonate, a salt of alkylphosphoric acid ester, an alkylaryl phosphate, a styrylaryl phosphate, a salt of polyoxyethylene alkyl ether sulfuric acid ester, a polyoxyethylene alkylaryl ether sulfate, a salt of polyoxyethylene alkylaryl ether sulfuric acid ester, a polyoxyethylene alkyl ether phosphate, a salt of polyoxyethylene alkylaryl phosphoric acid ester, a salt of polyoxyethylene aryl ether phosphoric acid ester, a naphthalene sulfonate condensed with formaldehyde or an alkylnaphthalene sulfonate condensed with formaldehyde; a nonionic surfactant such as a sorbitan fatty acid ester, a glycerin fatty acid ester, a fatty acid polyglyceride, a fatty acid alcohol polyglycol ether, acetylene glycol, acetylene alcohol, an oxyalkylene block polymer, a polyoxyethylene alkyl ether, a polyoxyethylene alkylaryl ether, a polyoxyethylene styrylaryl ether, a polyoxyethylene glycol alkyl ether, polyethylene glycol, a polyoxyethylene fatty acid ester, a polyoxyethylene sorbitan fatty acid ester, a polyoxyethylene glycerin fatty acid ester, a polyoxyethylene hydrogenated castor oil or a polyoxypropylene fatty acid ester; and a vegetable oil or mineral oil such as olive oil, kapok oil, castor oil, palm oil, camellia oil, coconut oil, sesame oil, corn oil, rice bran oil, peanut oil, cottonseed oil, soybean oil, rapeseed oil, linseed oil, tung oil or liquid paraffins. These additives may suitably be selected for use alone or in combination as a mixture of two or more of them, so long as the object of the present invention is met. Further, additives other than the above-mentioned may be suitably selected for use among those known in this field. For example, various additives commonly used, such as a filler, a thickener, an anti-settling agent, an anti-freezing agent, a dispersion stabilizer, a safener, an anti-mold agent, a bubble agent, a disintegrator and a binder, may be used. The mix ratio by weight of the compound of the present invention to such various additives may be from 0.1:99.9 to 95:5, preferably from 0.2:99.8 to 85:15.

The dose of the herbicide containing the compound of the present invention can not generally be defined, as it varies depending upon the weather conditions, the soil conditions, the type of the formulation, the type of the weeds to be controlled, the application season, etc. However, it is usually applied in an amount of the compound of the present invention of from 0.1 to 5,000 g, preferably from 0.5 to 1,000 g, more preferably from 1 to 500 g, per hectare. The present invention includes such a method for controlling undesired weeds, by such applications of the herbicide.

Further, the herbicide containing compound of the present invention may be mixed with or may be used in combination with other agricultural chemicals, fertilizers or phytotoxicity-reducing agents, whereby synergistic effects or activities may sometimes be obtained. Such other agricultural chemicals include, for example, a herbicide, a fungicide, an antibiotic, a plant hormone and an insecticide. Especially, with a mixed herbicidal composition having a compound of the present invention mixed with or used in combination with one or more active compounds of other herbicides, the range of weeds to be controlled, the time of application of the composition, the herbicidal activities, etc. may be improved to preferred directions. The compound of the present invention and the active compounds of other herbicides may separately be formulated so that they may be mixed for use at the time of application, or they may be formulated together. The present invention includes such a mixed herbicidal composition.

The mixing ratio of the compound of the present invention to the active compounds of other herbicides can not generally be defined, since it varies depending upon the weather conditions, the soil conditions, the types of formulations, the application time, the application method, etc., but the other herbicides are mixed in an amount of from 0.001 to 10,000 parts by weight, preferably from 0.01 to 1,000 parts by weight per one type of the active compound, based on 1 part by weight of the compound of the present invention. Further, the dose for the application is such that the total amount of the active compounds is from 0.1 to 10,000 g, preferably from 0.2 to 5,000 g, more preferably from 10 to 3,000 g, per hectare. The present invention includes a method for controlling undesired weeds by application of such a mixed herbicidal composition.

Another herbicidally active compound includes, for example, the following compounds (common names including ones under application for approval by ISO). Even when not specifically mentioned here, in a case where such compounds have salts, alkyl esters, etc., they are, of course, all included.

(1) Those which are believed to exhibit herbicidal effects by disturbing hormone activities of plants, such as a phenoxy type such as 2,4-D, 2,4-D-butotyl, 2,4-D-butyl, 2,4-D-dimethylammonium, 2,4-D-diolamine, 2,4-D-ethyl, 2,4-D-2-ethylhexyl, 2,4-D-isobutyl, 2,4-D-isoctyl, 2,4-D-isopropyl, 2,4-D-isopropylammonium, 2,4-D-sodium, 2,4-D-isopropanolammonium, 2,4-D-trolamine, 2,4-DB, 2,4-DB-butyl, 2,4-DB-dimethylammonium, 2,4-DB-isoctyl, 2,4-DB-potassium, 2,4-DB-sodium, dichlorprop, dichlorprop-butotyl, dichlorprop-dimethylammonium, dichlorprop-isoctyl, dichlorprop-potassium, dichlorprop-P, dichlorprop-P-dimethylammonium, dichlorprop-P-potassium, dichlorprop-P-sodium, MCPA, MCPA-butotyl, MCPA-dimethylammonium, MCPA-2-ethylhexyl, MCPA-potassium, MCPA-sodium, MCPA-thioethyl, MCPB, MCPB-ethyl, MCPB-sodium, mecoprop, mecoprop-butotyl, mecoprop-sodium, mecoprop-P, mecoprop-P-butotyl, mecoprop-P-dimethylammonium, mecoprop-P-2-ethylhexyl, mecoprop-P-potassium, naproanilide or clomeprop; an aromatic carboxylic acid type such as 2,3,6-TBA, dicamba, dicamba-butotyl, dicamba-diglycolamine, dicamba-dimethylammonium, dicamba-diolamine, dicamba-isopropylammonium, dicamba-potassium, dicamba-sodium, dichlobenil, picloram, picloram-dimethylammonium, picloram-isoctyl, picloram-potassium, picloram-triisopropanolammonium, picloram-triisopropylammonium, picloram-trolamine, triclopyr, triclopyr-butotyl, triclopyr-triethylammonium, clopyralid, clopyralid-olamine, clopyralid-potassium, clopyralid-triisopropanolammonium or aminopyralid; and others such as naptalam, naptalam-sodium, benazolin, benazolin-ethyl, quinclorac, quinmerac, diflufenzopyr, diflufenzopyr-sodium, fluoroxypyr, fluoroxypyr-2-butoxy-1-methylethyl, fluoroxypyr-meptyl, chlorflurenol or chlorflurenol-methyl.

(2) Those which are believed to exhibit herbicidal effects by inhibiting photosynthesis of plants, such as a urea type such as chlorotoluron, diuron, fluometuron, linuron, isoproturon, metobenzuron, tebuthiuron, dimefuron, isouron, karbutilate, methabenzthiazuron, metoxuron, monolinuron, neburon, siduron, terbumeton or trietazine; a triazine type such as simazine, atrazine, atratone, simetryn, prometryn, dimethametryn, hexazinone, metribuzin, terbuthylazine, cyanazine, ametryn, cybutryne, triaziflam, terbutryn, propazine, metamitron, prometon or indaziflam; a uracil type such as bromacil, bromacyl-lithium, lenacil or terbacil; an anilide type such as propanil or cypromid; a carbamate type such as swep, desmedipham or phenmedipham; a hydroxybenzonitrile type such as bromoxynil, bromoxynil-octanoate, bromoxynil-heptanoate, ioxynil, ioxynil-octanoate, ioxynil-potassium or ioxynil-sodium; and others such as pyridate, bentazone, bentazone-sodium, amicarbazone, methazole or pentanochlor.

(3) Quaternary ammonium salt type such as paraquat or diquat, which is believed to be converted to free radicals by itself to form active oxygen in the plant body and shows rapid herbicidal efficacy.

(4) Those which are believed to exhibit herbicidal effects by inhibiting chlorophyll biosynthesis of plants and abnormally accumulating a photosensitizing peroxide substance in the plant body, such as a diphenylether type such as nitrofen, chlomethoxyfen, bifenox, acifluorfen, acifluorfen-sodium, fomesafen, fomesafen-sodium, oxyfluorfen, lactofen, aclonifen, ethoxyfen-ethyl (HC-252), fluoroglycofen-ethyl or fluoroglycofen; a cyclic imide type such as chlorphthalim, flumioxazin, flumiclorac, flumiclorac-pentyl, cinidon-ethyl or fluthiacet-methyl; and others such as oxadiargyl, oxadiazon, sulfentrazone, carfentrazone-ethyl, thidiazimin, pentoxazone, azafenidin, isopropazole, pyraflufen-ethyl, benzfendizone, butafenacil, saflufenacil, flupoxam, fluazolate, profluazol, pyraclonil, flufenpyr-ethyl or bencarbazone.

(5) Those which are believed to exhibit herbicidal effects characterized by bleaching activities by inhibiting chromogenesis of plants such as carotenoids, such as a pyridazinone type such as norflurazon, chloridazon or mefflurazon; a pyrazole type such as pyrazolynate, pyrazoxyfen, benzofenap, topramezone (BAS-670H) or pyrasulfotole; and others such as amitrole, fluridone, flurtamone, diflufenican, methoxyphenone, clomazone, sulcotrione, mesotrione, tembotrione, tefuryltrione (AVH-301), isoxaflutole, difenzoquat, difenzoquat-metilsulfate, isoxachiortole, benzobicyclon, picolinafen or beflubutamid.

(6) Those which exhibit strong herbicidal effects specifically to gramineous plants, such as an aryloxyphenoxypropionic acid type such as diclofop-methyl, diclofop, pyriphenop-sodium, fluazifop-butyl, fluazifop, fluazifop-P, fluazifop-P-butyl, haloxyfop-methyl, haloxyfop, haloxyfop-etotyl, haloxyfop-P, haloxyfop-P-methyl, quizalofop-ethyl, quizalofop-P, quizalofop-P-ethyl, quizalofop-P-tefuryl, cyhalofop-butyl, fenoxaprop-ethyl, fenoxaprop-P, fenoxaprop-P-ethyl, metamifop-propyl, metamifop, clodinafop-propargyl, clodinafop or propaquizafop; a cyclohexanedione type such as alloxydim-sodium, alloxydim, clethodim, sethoxydim, tralkoxydim, butroxydim, tepraloxydim, profoxydim or cycloxydim; or others such as flamprop-M-methyl, flamprop-M or flamprop-M-isopropyl.

(7) Those which are believed to exhibit herbicidal effects by inhibiting an amino acid biosynthesis of plants, such as a sulfonylurea type such as chlorimuron-ethyl, chlorimuron, sulfometuron-methyl, sulfometuron, primisulfuron-methyl, primisulfuron, bensulfuron-methyl, bensulfuron, chiorsulfuron, metsulfuron-methyl, metsulfuron, cinosulfuron, pyrazosulfuron-ethyl, pyrazosulfuron, flazasulfuron, rimsulfuron, nicosulfuron, imazosulfuron, cyclosulfamuron, prosulfuron, azimsulfuron, flupyrsulfuron-methyl-sodium, flupyrsulfuron, triflusulfuron-methyl, triflusulfuron, halosulfuron-methyl, halosulfuron, thifensulfuron-methyl, thifensulfuron, ethoxysulfuron, oxasulfuron, ethametsulfuron, ethametsulfuron-methyl, iodosulfuron, iodosulfuron-methyl-sodium, sulfosulfuron, triasulfuron, tribenuron-methyl, tribenuron, tritosulfuron, foramsulfuron, trifloxysulfuron, trifloxysulfuron-sodium, mesosulfuron-methyl, mesosulfuron, orthosulfamuron, flucetosulfuron, amidosulfuron, propyrisulfuron (TH-547), NC-620, a compound disclosed in WO2005092104; a triazolopyrimidinesulfonamide type such as flumetsulam, metosulam, diclosulam, cloransulam-methyl, florasulam, penoxsulam or pyroxsulam; an imidazolinone type such as imazapyr, imazapyr-isopropylammonium, imazethapyr, imazethapyr-ammonium, imazaquin, imazaquin-ammonium, imazamox, imazamox-ammonium, imazamethabenz, imazamethabenz-methyl or imazapic; a pyrimidinylsalicylic acid type such as pyrithiobac-sodium, bispyribac-sodium, pyriminobac-methyl, pyribenzoxim, pyriftalid, pyrimisulfan (KUH-021); a sulfonylaminocarbonyltriazolinone type such as flucarbazone, flucarbazone-sodium, propoxycarbazone-sodium or propoxycarbazone; and others such as glyphosate, glyphosate-sodium, glyphosate-potassium, glyphosate-ammonium, glyphosate-diammonium, glyphosate-isopropylammonium, glyphosate-trimesium, glyphosate-sesquisodium, glufosinate, glufosinate-ammonium, glufosinate-P, glufosinate-P-ammonium, glufosinate-P-sodium, bilanafos, bilanafos-sodium or cinmethylin.

(8) Those which are believed to exhibit herbicidal effects by inhibiting cell mitoses of plants, such as a dinitroaniline type such as trifluralin, oryzalin, nitralin, pendimethalin, ethalfluralin, benfluralin, prodiamine, butralin or dinitramine; an amide type such as bensulide, napropamide, propyzamide or pronamide; an organic phosphorus type such as amiprofos-methyl, butamifos, anilofos or piperophos; a phenyl carbamate type such as propham, chlorpropham, barban or carbetamide; a cumylamine type such as daimuron, cumyluron, bromobutide or methyldymron; and others such as asulam, asulam-sodium, dithiopyr, thiazopyr, chlorthal-dimethyl, chlorthal or diphenamid.

(9) Those which are believed to exhibit herbicidal effects by inhibiting protein biosynthesis or lipid biosynthesis of plants, such as a chloroacetamide type such as alachlor, metazachlor, butachlor, pretilachlor, metolachlor, S-metolachlor, thenylchlor, pethoxamid, acetochlor, propachlor, dimethenamid, dimethenamid-P, propisochloror dimethachlor; a thiocarbamate type such as molinate, dimepiperate, pyributicarb, EPTC, butylate, vernolate, pebulate, cycloate, prosulfocarb, esprocarb, thiobencarb, diallate, tri-allate or orbencarb; and others such as etobenzanid, mefenacet, flufenacet, tridiphane, cafenstrole, fentrazamide, oxaziclomefone, indanofan, benfuresate, pyroxasulfone (KIH-485), dalapon, dalapon-sodium, TCA-sodium or trichloroacetic acid.

(10) MSMA, DSMA, CMA, endothall, endothall-dipotassium, endothall-sodium, endothall-mono(N,N-dimethylalkylammonium), ethofumesate, sodium chlorate, pelargonic acid, nonanoic acid, fosamine, fosamine-ammonium, pinoxaden, ipfencarbazone (HOK-201), aclolein, ammonium sulfamate, borax, chloroacetic acid, sodium chloroacete, cyanamide, methylarsonic acid, dimethylarsinic acid, sodium dimethylarsinate, dinoterb, dinoterb-ammonium, dinoterb-diolamine, dinoterb-acetate, DNOC, ferrous sulfate, flupropanate, flupropanate-sodium, isoxaben, mefluidide, mefluidide-diolamine, metam, metam-ammonium, metam-potassium, metam-sodium, methyl isothiocyanate, pentachlorophenol, sodium pentachlorophenoxide, pentachlorophenol laurate, quinoclamine, sulfuric acid, urea sulfate, etc.

(11) Those which are believed to exhibit herbicidal effects by being parasitic on plants, such as *Xanthomonas campestris, Epicoccosirus nematosorus, Epicoccosirus nematosperus, Exserohilum monoseras* or *Drechsrela monoceras*.

Now, examples of preferred embodiments of the present invention will be given below, but it should be understood that the present invention is by no means restricted thereto.

(1) 1-(4-(3-(Ethoxymethyl)-2-methyl-4-(methylsulfonyl)benzoyl)-1-methyl-1H-pyrazol-5-yloxy)ethyl methyl carbonate (the following Compound No. 1-1)

(2) Methyl 3-(5-(1-(methoxycarbonyloxy)ethoxy)-1-methyl-1H-pyrazole-4-carbonyl)-2-methyl-6-(methylsulfonyl)benzoate (the following Compound No. 1-2)

(3) 1-(4-(3-(Methoxymethyl)-2-methyl-4-(methylsulfonyl)benzoyl)-1-methyl-1H-pyrazol-5-yloxy)ethyl methyl carbonate (the following Compound No. 1-3)

(4) 1-(4-(3-(Ethoxymethyl)-2-methyl-4-(methylsulfonyl)benzoyl)-1-methyl-1H-pyrazol-5-yloxy)ethyl ethyl carbonate (the following Compound No. 1-4)

(5) Ethyl 1-(4-(3-(2-isopropoxyethoxy)-2-methyl-4-(methylsulfonyl)benzoyl)-1-methyl-1H-pyrazol-5-yloxy)ethyl carbonate (the following Compound No. 1-5)

(6) 1-(4-(3-(2-Methoxyethoxy)-2-methyl-4-(methylsulfonyl)benzoyl)-1,3-dimethyl-1H-pyrazol-5-yloxy)ethyl methyl carbonate (the following Compound No. 1-6)

(7) 1-(1-Ethyl-4-(3-(2-methoxyethoxy)-2-methyl-4-(methylsulfonyl)benzoyl)-1H-pyrazol-5-yloxy)ethyl methyl carbonate (the following Compound No. 2-1)

(8) Methyl 3-(5-(1-(methoxycarbonyloxy)ethoxy)-1-ethyl-1H-pyrazole-4-carbonyl)-2-methyl-6-(methylsulfonyl)benzoate (the following Compound No. 2-2)

(9) Ethyl 1-(1-ethyl-4-(3-(2-methoxyethoxy)-2-methyl-4-(methylsulfonyl)benzoyl)-3-methyl-1H-pyrazol-5-yloxy)ethyl carbonate (the following Compound No. 2-3)

(10) Ethyl 1-(1-n-propyl-4-(3-(2-methoxyethoxy)-2-methyl-4-(methylsulfonyl)benzoyl)-1H-pyrazol-5-yloxy)ethyl carbonate (the following Compound No. 3-1)

(11) 1-(1-Isopropyl-4-(3-(2-methoxyethoxy)-2-methyl-4-(methylsulfonyl)benzoyl)-1H-pyrazol-5-yloxy)ethyl methyl carbonate (the following Compound No. 4-1)

(12) (5-Hydroxy-1-methyl-1H-pyrazol-4-yl)(3-(2-isopropylethoxy)-2-methyl-4-(methylsulfonyl)phenyl)ketone (the following Compound No. 5-1)

(13) (5-Hydroxy-1,3-dimethyl-1H-pyrazol-4-yl)(3-(2-methoxyethoxy)-2-methyl-4-(methylsulfonyl)phenyl)ketone (the following Compound No. 5-2)

(14) (5-Hydroxy-1-methyl-3-ethyl-1H-pyrazol-4-yl)(3-(2-methoxyethoxy)-2-methyl-4-(methylsulfonyl)phenyl)ketone (the following Compound No. 5-3)

(15) (1-Ethyl-5-hydroxy-3-methyl-1H-pyrazol-4-yl)(3-(2-methoxyethoxy)-2-methyl-4-(methylsulfonyl)phenyl)ketone (the following Compound No. 6-1)

(16) (5-Hydroxy-1-n-propyl-1H-pyrazol-4-yl)(3-(2-methoxyethoxy)-2-methyl-4-(methylsulfonyl)phenyl)ketone (the following Compound No. 7-1)

(17) (5-Hydroxy-1-isopropyl-1H-pyrazol-4-yl)(3-(2-methoxyethoxy)-2-methyl-4-(methylsulfonyl)phenyl)ketone (the following Compound No. 8-1)

(18) (5-Hydroxy-1-isopropyl-3-methyl-1H-pyrazol-4-yl)(3-(2-methoxyethoxy)-2-methyl-4-(methylsulfonyl)phenyl)ketone (the following Compound No. 8-2)

(19) Metal salt of (5-hydroxy-1-ethyl-1H-pyrazol-4-yl)(3-(2-methoxyethoxy)-2-methyl-4-(methylsulfonyl)phenyl)ketone

(20) Potassium salt of (5-hydroxy-1-ethyl-1H-pyrazol-4-yl)(3-(2-methoxyethoxy)-2-methyl-4-(methylsulfonyl)phenyl)ketone

(21) Sodium salt of (5-hydroxy-1-ethyl-1H-pyrazol-4-yl) (3-(2-methoxyethoxy)-2-methyl-4-(methylsulfonyl)phenyl) ketone

(22) A herbicidal composition comprising a pyrazole compound of the above (1) to (21) or its salt, and an agricultural adjuvant.

(23) A method for controlling undesired plants or inhibiting their growth, which comprises applying a herbicidally effective amount of the pyrazole compound of the above (1) to (21) or its salt to the undesired plants or to a place where they grow.

(24) The method of the above (23), wherein the undesired plants are controlled or their growth is inhibited in a corn field.

(25) The method of the above (24), wherein the corn is a transformed one.

(26) The method of the above (23), wherein the undesired plants are controlled or their growth is inhibited in a wheat, a barley, or a rye field.

(27) The method of the above (23), wherein the undesired plants are controlled or their growth is inhibited in a rice field.

(28) The method of the above (23), wherein the undesired plants are controlled or their growth is inhibited in a non-agricultural field.

(29) A process for producing a pyrazole compound represented by the formula (I) or its salt:

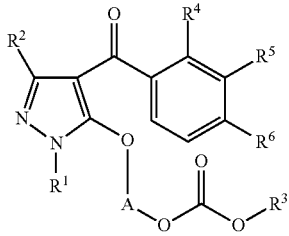
(I)

wherein $R^1$, $R^2$, $R^3$, $R^4$, $R^5$, $R^6$ and A are as defined above, which comprises reacting a pyrazole compound represented by the formula (II) or its salt:

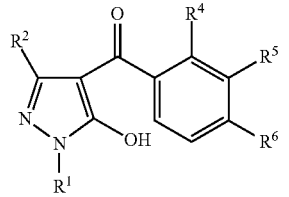
(II)

wherein $R^1$, $R^2$, $R^4$, $R^5$ and $R^6$ are as defined above, with a compound represented by the formula (III):

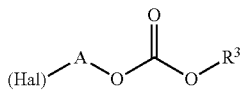
(III)

wherein $R^3$, Hal and A are as defined above.

(30) The process of the above (29), which is carried out in the presence of n-tetrabutylammonium bromide and an aromatic solvent.

(31) The process of the above (30) wherein the aromatic solvent is toluene.

(32) A process for producing a pyrazole compound represented by the formula (II):

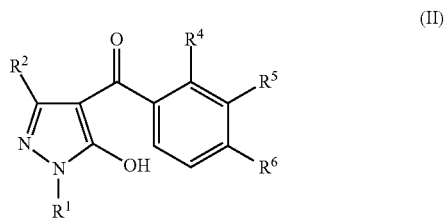
(II)

wherein $R^1$, $R^2$, $R^4$, $R^5$ and $R^6$ are as defined above, or its salt, which comprises subjecting a compound represented by the formula (IV):

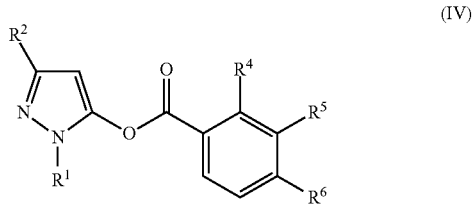
(IV)

wherein $R^1$, $R^2$, $R^4$, $R^5$ and $R^6$ are as defined above, to a rearrangement reaction in the presence of an alkali metal carbonate and an aromatic solvent.

(33) The process of the above (32), wherein the alkali metal carbonate is potassium carbonate.

(34) The process of the above (32), wherein the aromatic solvent is toluene.

(35) The process of the above (32), wherein the salt of the formula (II) is a potassium salt.

(36) A process for producing a compound represented by the formula (IV):

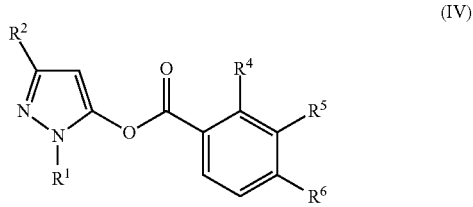
(IV)

wherein $R^1$, $R^2$, $R^4$, $R^5$ and $R^6$ are as defined above, which comprises reacting a compound represented by the formula (VI):

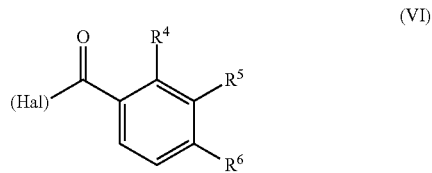
(VI)

wherein $R^4$, $R^5$, $R^6$ and Hal are as defined above, with a compound represented by the formula (V):

(V)

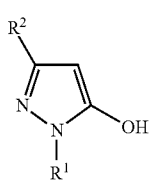

wherein $R^1$ and $R^2$ are as defined above, or its salt, in the presence of a base and an aromatic solvent.

(37) The process of the above (36), wherein the base is triethylamine.

(38) The process of the above (36), wherein the aromatic solvent is toluene.

(39) A process for producing the compound represented by the formula (VI):

(VI)

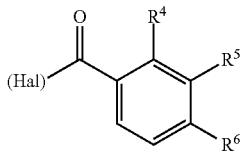

wherein $R^4$, $R^5$, $R^6$ and Hal are defined above, which comprises reacting a compound represented by the formula (VII):

(VII)

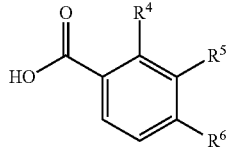

wherein $R^4$, $R^5$ and $R^6$ are as defined above, with a halogenating agent in the presence of an aromatic solvent.

(40) The process of the above (39), wherein the halogenating agent is thionyl chloride.

(41) The process of the above (39), wherein the aromatic solvent is toluene.

(42) A process for producing the compound represented by the formula (VII):

(VII)

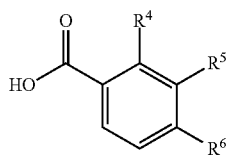

wherein $R^4$, $R^5$ and $R^6$ are as defined above, which comprises reacting a compound represented by the formula (XVII):

(XVII)

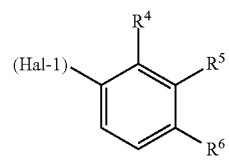

wherein $R^4$, $R^5$, $R^6$ and Hal-1 are as defined above, with carbon monoxide or its equivalent, and $H_2O$, in the presence of a catalyst and a base by using a $C_4$ alcohol as a solvent.

(43) The process of the above (42), wherein the $C_4$ alcohol is tert-butyl alcohol.

(44) A process for producing a compound represented by the formula (XVII-a):

(XVII-a)

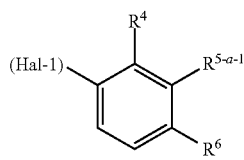

wherein Hal-1, $R^4$, $R^6$ and $R^{5-a-1}$ are as defined above, which comprises reacting a compound represented by the formula (XVIII):

(XVIII)

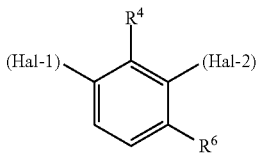

wherein $R^4$, $R^6$, Hal-1 and Hal-2 are as defined above, with a compound represented by the formula (XIX): HO—$R^\alpha$ wherein $R^\alpha$ is as defined above, in the presence of an alkali metal hydroxide and an aromatic solvent.

(45) The process of the above (44), wherein the alkali metal hydroxide is sodium hydroxide.

(46) The process of the above (44), wherein the aromatic solvent is toluene.

(47) A process for producing a compound represented by the formula (XVIII):

(XVIII)

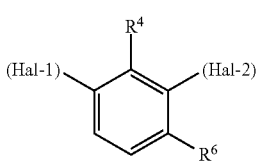

wherein Hal-1, Hal-2, $R^4$ and $R^6$ are as defined above, which comprises reacting a compound represented by the formula (XX):

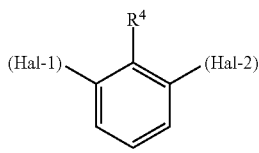

wherein $R^4$, Hal-1 and Hal-2 are as defined above, with ($R^6$) (Hal-3), wherein $R^6$ and Hal-3 are as defined above, in the presence of iron chloride.

(48) A process for obtaining a product of a compound represented by the formula (XVIII):

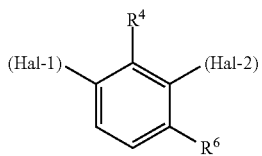

wherein $R^4$, $R^6$, Hal-1 and Hal-2 are as defined above, and Hal-1 and Hal-2 may be the same or different from each other, which comprises adding an inorganic acid and an alcohol solvent simultaneously or separately to a mixture comprising the compound represented by the formula (XVIII) and an acid.

(49) The process of the above (48), wherein the mixture in the above (48) is one obtained by the reaction of (47).

(50) The process of the above (48), wherein the inorganic acid is hydrochloric acid.

(51) The process of the above (50), wherein the alcohol solvent is a $C_3$ alcohol.

EXAMPLES

Now, the present invention will be described with reference to Examples. However, it should be understood that the present invention is by no means restricted to such specific Examples. Preparation Examples for the Compounds of the Present Invention Will be Described Below.

Preparation Example 1

Preparation of 1-(1-ethyl-4-(3-(2-methoxyethoxy)-2-methyl-4-(methylsulfonyl)benzoyl)-1H-pyrazol-5-yloxy)ethyl methyl carbonate (the following Compound No. 2-1)

5-Hydroxy-1-ethylpyrazol-4-yl 3-(2-methoxyethoxy)-2-methyl-4-(methylsulfonyl)phenyl ketone (300 mg) was dissolved in 2-butanone (10 mL), and potassium carbonate (130 mg) and tetrabutylammonium bromide (15 mg) were added. After stirring at room temperature for 10 minutes, 1-chloroethyl methyl carbonate (purity: 85%, 270 mg) was added at room temperature, followed by heating and refluxing for 3 hours. After completion of the reaction, the reaction mixture was cooled to room temperature and poured into water and then extracted with ethyl acetate. The organic layer was washed with 1N hydrochloric acid and a saturated sodium chloride aqueous solution, followed by drying over anhydrous sodium sulfate. The solvent was distilled off under reduced pressure. The obtained residue was purified by column chromatography with n-hexane:ethyl acetate=1:1, to obtain the desired product (180 mg) as slightly yellow solid.

Preparation Example 2

Preparation of 1-(1,3-dimethyl-4-(3-(2-methoxyethoxy)-2-methyl-4-(methylsulfonyl)benzoyl)-1H-pyrazol-5-yloxy)ethyl methyl carbonate (the following Compound No. 1-6)

(1) 3-(2-Methoxyethoxy)-2-methyl-4-(methylsulfonyl)benzoic acid (1 g) was dissolved in chloroform (20 mL), and oxalyl chloride (500 mg) was added. A catalytic amount of dimethylformamide was added, followed by stirring at room temperature for 3 hours. Then, the solvent was distilled off under reduced pressure. The obtained residue was dissolved in tetrahydrofuran (5 mL), and then a solution having 5-hydroxy-1,3-dimethylpyrazole (450 mg) dissolved in tetrahydrofuran (15 mL) was slowly added. Triethylamine (0.65 mL) was added, followed by heating and refluxing for 5 hours. After completion of the reaction, the reaction mixture was cooled to room temperature and poured into water, then acidified with dilute hydrochloric acid and then extracted with ethyl acetate. The organic layer was washed with a saturated sodium chloride aqueous solution and then dried over magnesium sulfate. The solvent was distilled off under reduced pressure.

The obtained residue was dissolved in acetonitrile (20 mL), and under cooling in an ice bath, triethylamine (0.65 mL) and acetone cyanohydrin (100 mg) were added, followed by stirring at room temperature for 18 hours. The reaction solution was poured into water and washed with a small amount of ethyl acetate. Then, the aqueous layer was acidified with dilute hydrochloric acid. It was extracted with ethyl acetate, and then, the organic layer was washed with a saturated sodium chloride aqueous solution and then dried over magnesium sulfate. The solvent was distilled off under reduced pressure. The obtained residue was purified by column chromatography (developing solvent: ethyl acetate) to obtain 5-hydroxy-1,3-dimethylpyrazol-4-yl 3-(2-methoxyethoxy)-2-methyl-4-(methylsulfonyl)phenyl ketone (500 mg, the following Compound No. 5-2) as slightly yellow solid.

(2) 5-Hydroxy-1,3-dimethylpyrazol-4-yl 3-(2-methoxyethoxy)-2-methyl-4-(methylsulfonyl)phenyl ketone (300 mg) was dissolved in 2-butanone (10 mL), and potassium carbonate (130 mg) and tetrabutyl ammonium bromide (15 mg) were added. After stirring at room temperature for 10 minutes, 1-chloroethyl methyl carbonate (purity: 85%, 270 mg) was added at room temperature, followed by heating and refluxing for 3 hours. After completion of the reaction, the reaction solution was cooled to room temperature and poured into water and then extracted with ethyl acetate. The organic layer was washed with a 1N hydrochloric solution and a saturated sodium chloride aqueous solution and then dried over anhydrous sodium sulfate. The solvent was distilled off under reduced pressure. The obtained residue was purified by column chromatography (n-hexane:ethyl acetate=1:1) to obtain the desired product (200 mg) as slightly yellow solid.

Preparation Example 3

Preparation of 1-(1-ethyl-4-(3-(2-methoxyethoxy)-2-methyl-4-(methylsulfonyl)benzoyl)-1H-pyrazol-5-yloxy)ethyl methyl carbonate (1) 2,6-Dichlorotoluene (100 g) and methanesulfonyl chloride (85.3 g) were mixed and heated to 80° C. Then, iron(III)

chloride (101 g) was added, and the mixture was further heated to 120° C. and stirred under heating for 6 hours. After completion of the reaction, the reaction mixture was cooled to 90° C., and then 10% hydrochloric acid (230 mL) was slowly added so that the temperature of the reaction mixture would not rapidly be lowered and solidified, and at 80° C., isopropanol (230 mL) was further added slowly. The mixture was cooled to room temperature, and then, with vigorous stirring, seed crystals of 1,3-dichloro-2-methyl-4-(methylsulfonyl)benzene were added to have solid precipitated. The precipitated solid was collected by filtration and washed with a solvent (water:isopropanol=1:1, 300 mL). The obtained solid was dissolved in ethyl acetate (600 mL) under heating, followed by filtration to remove insolubles. The filtrate was concentrated to obtain 1,3-dichloro-2-methyl-4-(methylsulfonyl)benzene (105 g) as slightly yellow solid.

$^1$H-NMR 400 MHz (CDCl$_3$ δ ppm): 2.57 (3H, s), 3.28 (3H, s), 7.50 (1H, d, J=8.4 Hz), 7.97 (1H, d, J=8.4 Hz).

(2) 1,3-Dichloro-2-methyl-4-(methylsulfonyl)benzene (13.1 g) and toluene (40 mL) were mixed, and 2-methoxyethanol (4.49 g) and sodium hydroxide (4.55 g) were added, followed by heating and refluxing for 3 hours. After completion of the reaction, the mixture was cooled to room temperature, and the solvent was distilled off under reduced pressure. To the obtained residue, a mixed solvent of methanol (12 mL) and water (48 mL) was added, followed by stirring for a while. Then, the formed solid was collected by filtration, further washed with water and dried to obtain 1-chloro-3-(2-methoxyethoxy)-2-methyl-4-(methylsulfonyl)benzene (12.4 g) as slightly yellow solid.

$^1$H-NMR 300 MHz (CDCl$_3$ δ ppm): 2.41 (3H, s), 3.25 (3H, s), 3.48 (3H, s), 3.78-3.81 (2H, m), 4.20-4.22 (2H, m), 7.33 (1H, d, J=8.4 Hz), 7.76 (1H, d, J=8.7 Hz).

(3) 12.5 mL of water was added to 237.5 mL of tert-butanol, then nitrogen gas was blown thereinto for 5 minutes to remove dissolved oxygen thereby to prepare a reaction solvent. Into a 500 mL autoclave, 50.0 g of 1-chloro-3-(2-methoxyethoxy)-2-methyl-4-(methylsulfonyl)benzene, 28.5 g of sodium carbonate, 1.5 g of 1,4-bis(diphenylphosphino)butane, the above reaction solvent, and 1.5 g of 5% Pd/C were introduced, and the autoclave was closed. With stirring, nitrogen flushing (5.0 MPa) was carried out twice, followed by flushing with carbon monoxide (5.0 MPa) twice. Finally, carbon monoxide was filled (2.5 MPa). By an electric furnace, the autoclave was heated to 160° C., followed by stirring for 7 hours (300 rps). After cooling to room temperature, carbon monoxide gas remaining in the autoclave was removed. The content was poured into water and ethyl acetate, and insolubles were filtered off by celite. Then, the filtrate was subjected to liquid separation, and the aqueous layer was washed twice with ethyl acetate. The aqueous layer was acidified with hydrochloric acid (pH=1) and then extracted with ethyl acetate. The organic layer was washed with a saturated sodium chloride aqueous solution and dried over sodium sulfate, and then, the solvent was distilled off under reduced pressure to obtain 3-(2-methoxyethoxy)-2-methyl-4-(methylsulfonyl)benzoic acid (50.1 g). Further, the obtained solid was washed with 150 mL of hexane and then collected by filtration and dried under reduced pressure to obtain 3-(2-methoxyethoxy)-2-methyl-4-(methylsulfonyl)benzoic acid (48.1 g) as white solid.

$^1$H-NMR 300 MHz (CDCl$_3$ δ ppm): 2.63 (3H, s), 3.31 (3H, s), 3.50 (3H, s), 3.82-3.85 (2H, m), 4.22-4.25 (2H, m), 7.92 (2H, s).

(4) 3-(2-Methoxyethoxy)-2-methyl-4-(methylsulfonyl)benzoic acid (100 g) and toluene (300 mL) were mixed, and thionyl chloride (47.5 g) and DMF (2.5 g) were added, followed by heating and stirring at 100° C. for 2 hours. After completion of the reaction, 180 mL of toluene was distilled off under reduced pressure to obtain a solution of 3-(2-methoxyethoxy)-2-methyl-4-(methylsulfonyl)benzoyl chloride.

(5) To 1-ethyl-5-hydroxypyrazole (42.8 g), toluene (150 mL) and triethylamine (38.6 g) were added to obtain a uniform solution, and while maintaining the solution at a temperature of at most 30° C., the acid chloride solution obtained in the above (4) was dropwise added. The interior of the container was further washed with toluene (20 mL), and the remaining acid chloride solution was dropwise added to the reaction solution. After stirring at room temperature for 1 hour, stirring was further carried out at 80° C. for 0.5 hour. The reaction solution was cooled to room temperature and then poured into water (150 mL) for liquid separation. The aqueous layer after the liquid separation was extracted once with toluene (200 mL) and washed with a small amount of a saturated sodium chloride aqueous solution. Then, the organic layer was put together and dried over magnesium sulfate. Magnesium sulfate was filtered off, followed by washing with toluene (50 mL) to obtain a toluene solution of 1-ethyl-1H-pyrazol-5-yl 3-(2-methoxyethoxy)-2-methyl-4-(methylsulfonyl)benzoate.

From the toluene solution, a very small amount was sampled, and toluene was distilled off from the solution, and its $^1$H-NMR spectrum was measured to confirm its formation.

$^1$H-NMR 400 MHz (CDCl$_3$ δ ppm): 1.46 (3H, t, J=7.6 Hz), 2.64 (3H, s), 3.31 (3H, s), 3.48 (3H, s), 3.81 (2H, t, J=4.4 Hz), 4.16 (2H, q, J=7.6 Hz), 4.24 (2H, t, J=4.4 Hz), 6.30 (1H, d, J=2.0 Hz), 7.53 (1H, d, J=2.0 Hz), 7.95 (1H, d, J=8.4 Hz), 7.97 (1H, d, J=8.4 Hz).

(6) The toluene solution obtained in (5) was transferred to a container equipped with an azeotropic dehydration apparatus, and a part of toluene (about 100 mL) was distilled off together with included water. The solution was cooled to 80° C., and then DMF (40 mL) and powdery potassium carbonate (33.6 g) were added. With vigorous stirring, heating and refluxing were carried out, and toluene (about 100 mL) was distilled off by azeotropic dehydration. The azeotropic dehydration was carried out for 3 hours, and then a part of the solvent was distilled off under reduced pressure to obtain a toluene solution containing a potassium salt of (5-hydroxy-1-ethylpyrazol-4-yl)(3-(2-methoxyethoxy)-2-methyl-4-(methylsulfonyl)phenyl)ketone.

(7) Chloroformic acid 1-chloroethyl ester (250 g) was dissolved in diethyl ether (1 L), and under cooling with ice, methanol (59 g) and triethylamine (195 g) were sequentially dropwise added. After completion of the dropwise addition, stirring was carried out at room temperature for 1 hour. Into the system, water (250 mL) was added for liquid separation, and the organic layer was washed with dilute hydrochloric acid. The residue obtained by distilling the solvent off, was subjected to distillation under reduced pressure to obtain 1-chloroethyl methyl carbonate (217.6 g, b.p. 85-90° C./0.085-0.093 MPa).

$^1$H-NMR 400 MHz (CDCl$_3$ δ ppm): 1.79 (3H, d, J=4.4 Hz), 3.82 (3H, s), 6.39 (1H, q, J=6.0 Hz).

(8) The toluene solution obtained in (6) was cooled to 90° C., and tetra-n-butylammonium bromide (5.6 g) was added, and 1-chloroethyl methyl carbonate (62.5 g) was slowly dropwise added. After completion of the dropwise addition, the reaction solution was stirred at 100° C. for 3 hours, and then cooled to 50° C. Hexane (150 mL) was added thereto, followed by stirring for 30 minutes. Further, water (100 mL) and 3N hydrochloric acid (100 mL) were sequentially added, followed by to stirring at room temperature for 30 minutes. Precipitated crystals were collected by filtration, washed with water and further washed with a mixed liquid (300 mL) of hexane:toluene=1:2, to obtain the dried desired product (120.9 g) as slightly brown solid.

Preparation Example 4

Preparation of 1-(1-ethyl-4-(3-(2-methoxyethoxy)-2-methyl-4-(methylsulfonyl)benzoyl)-1H-pyrazol-5-yloxy)ethyl methyl carbonate (1) In methanol (20 mL), 5-hydroxy-1-ethylpyrazol-4-yl 3-(2-methoxyethoxy)-2-methyl-4-(methylsulfonyl)phenyl ketone (1 g) and potassium hydroxide (180 mg) were mixed, followed by heating and refluxing for 1 hour. The obtained solution was cooled to room temperature, and then the solvent was distilled off under reduced pressure to obtain a potassium salt of (1-ethyl-5-hydroxypyrazol-4-yl)(3-(2-methoxyethoxy-2-methyl-4-(methylsulfonyl)phenyl)ketone (1 g) as slightly brown oil.

$^1$H-NMR 400 MHz (CD$_3$OD δ ppm): 1.21 (3H, t, J=7.2 Hz), 2.27 (3H, s), 3.27 (3H, s), 3.42 (3H, s), 3.76 (4H, m), 4.19 (2H, m), 7.15 (1H, d, J=7.6 Hz), 7.75 (1H, d, J=7.6 Hz).

(2) The potassium salt of (5-hydroxy-1-ethylpyrazol-4-yl)(3-(2-methoxyethoxy)-2-methyl-4-(methylsulfonyl)phenyl) ketone (1 g) obtained in (1) is dissolved in 2-butanone (10 mL), and tetrabutylammonium bromide (15 mg) is added. Thereafter, the reaction is carried out in the same manner as in Preparation Example 1 to obtain the desired product.

Preparation Example 5

Preparation of 1-(1-ethyl-4-(3-(2-methoxyethoxy)-2-methyl-4-(methylsulfonyl)benzoyl)-1H-pyrazol-5-yloxy)ethyl methyl carbonate (1) A sodium salt of (1-ethyl-5-hydroxypyrazol-4-yl)(3-(2-methoxyethoxy-2-methyl-4-(methylsulfonyl)phenyl)ketone (1 g) was obtained by carrying out the reaction in the same manner as in Preparation Example 4 except that potassium hydroxide in the above Preparation Example 4 was changed to sodium hydroxide.

$^1$H-NMR 400 MHz (CD$_3$OD δ ppm): 1.20 (3H, t, J=7.2 Hz), 2.27 (3H, s), 3.26 (3H, s), 3.42 (3H, s), 3.74 (2H, q, J=7.2 Hz), 3.77 (2H, m), 4.18 (2H, m), 7.16 (1H, d, J=8.4 Hz), 7.74 (1H, d, J=8.4 Hz).

(2) The sodium salt (300 mg) of (1-ethyl-5-hydroxypyrazol-4-yl)(3-(2-methoxyethoxy-2-methyl-4-(methylsulfonyl)phenyl)ketone (1 g) obtained in (1) is reacted in the same manner as in the above Preparation Example 4(2) to obtain the desired product.

Preparation Example 6

Preparation of 1-(1-ethyl-4-(3-(2-methoxyethoxy)-2-methyl-4-(methylsulfonyl)benzoyl)-1H-pyrazol-5-yloxy)ethyl methyl carbonate (1) 3-(2-Methoxyethoxy)-2-methyl-4-(methylsulfonyl) benzoic acid (500 mg) was dissolved in chloroform (20 mL), and oxalyl chloride (500 mg) and a catalytic amount of DMF were added, followed by stirring at room temperature for 3 hours. Under reduced pressure, the solvent and an excess reagent were distilled off to obtain 3-(2-methoxyethoxy)-2-methyl-4-(methylsulfonyl)benzoyl chloride (520 mg) as an oily product.

$^1$H-NMR 400 MHz (CDCl$_3$ δ ppm): 2.50 (3H, s), 3.26 (3H, s), 3.44 (3H, s), 3.77 (2H, m), 4.18 (2H, m), 7.92, (1H, d, J=8.8 Hz), 7.96 (1H, d, J=8.8 Hz).

(2) A toluene solution of 3-(2-methoxyethoxy)-2-methyl-4-(methylsulfonyl)benzoyl chloride obtained in the above (1) is prepared and reacted in the same manner as in the above Preparation Example 3 (5) et. seq to obtain the desired product.

Now, typical examples of the compounds of the present invention are shown in Tables 1 to 8, and their $^1$H-NMR spectrum data are shown in Table 9. These compounds can be prepared in accordance with the above Preparation Examples or the above-mentioned various processes. Here, in Tables 1 to 9, No. represents the Compound No. Further, in Tables, Me represents a methyl group, Et an ethyl group, n-Pr a n-propyl group, and i-Pr an isopropyl group. Further, the left side of -A- is bonded to the pyrazole side, and the right side of -A- is bonded to the carbonate side.

TABLE 1

($R^1$ = Me, $R^6$ = SO$_2$Me)

| No. | $R^2$ | $R^3$ | $R^4$ | $R^5$ | —A— |
|-----|-------|-------|-------|-------|------|
| 1-1 | H | Me | Me | CH$_2$OEt | —CH(Me)— |
| 1-2 | H | Me | Me | C(O)OMe | —CH(Me)— |
| 1-3 | H | Me | Me | CH$_2$OMe | —CH(Me)— |
| 1-4 | H | Et | Me | CH$_2$OEt | —CH(Me)— |
| 1-5 | H | Et | Me | OCH$_2$CH$_2$OCH(Me)$_2$ | —CH(Me)— |
| 1-6 | Me | Me | Me | OCH$_2$CH$_2$OMe | —CH(Me)— |

TABLE 2

($R^1$ = Et, $R^6$ = SO$_2$Me)

| No. | $R^2$ | $R^3$ | $R^4$ | $R^5$ | —A— |
|-----|-------|-------|-------|-------|------|
| 2-1 | H | Me | Me | OCH$_2$CH$_2$OMe | —CH(Me)— |
| 2-2 | H | Et | Me | C(O)OMe | —CH(Me)— |
| 2-3 | Me | Et | Me | OCH$_2$CH$_2$OMe | —CH(Me)— |

TABLE 3

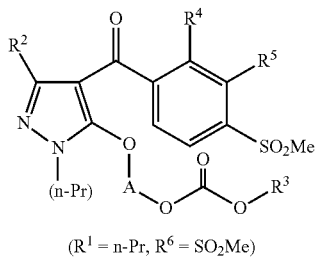

($R^1$ = n-Pr, $R^6$ = $SO_2Me$)

| No. | $R^2$ | $R^3$ | $R^4$ | $R^5$ | —A— |
|---|---|---|---|---|---|
| 3-1 | H | Et | Me | $OCH_2CH_2OMe$ | —CH(Me)— |

TABLE 4

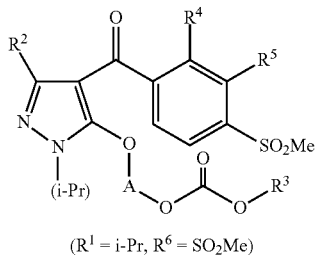

($R^1$ = i-Pr, $R^6$ = $SO_2Me$)

| No. | $R^2$ | $R^3$ | $R^4$ | $R^5$ | —A— |
|---|---|---|---|---|---|
| 4-1 | H | Me | Me | $OCH_2CH_2OMe$ | —CH(Me)— |

TABLE 5

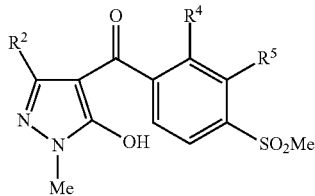

($R^1$ = Me, $R^6$ = $SO_2Me$)

| No. | $R^2$ | $R^4$ | $R^5$ |
|---|---|---|---|
| 5-1 | H | Me | $OCH_2CH_2OCH(Me)_2$ |
| 5-2 | Me | Me | $OCH_2CH_2OMe$ |
| 5-3 | Et | Me | $OCH_2CH_2OMe$ |

TABLE 6

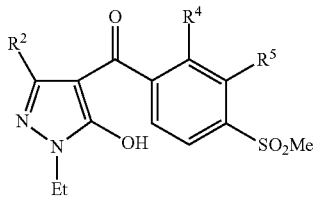

($R^1$ = Et, $R^6$ = $SO_2Me$)

| No. | $R^2$ | $R^4$ | $R^5$ |
|---|---|---|---|
| 6-1 | Me | Me | $OCH_2CH_2OMe$ |

TABLE 7

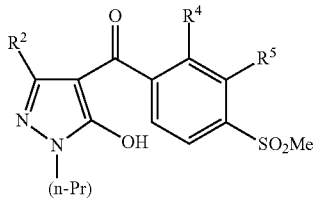

($R^1$ = n-Pr, $R^6$ = $SO_2Me$)

| No. | $R^2$ | $R^4$ | $R^5$ |
|---|---|---|---|
| 7-1 | H | Me | $OCH_2CH_2OMe$ |

TABLE 8

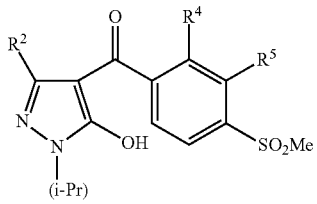

($R^1$ = i-Pr, $R^6$ = $SO_2Me$)

| No. | $R^2$ | $R^4$ | $R^5$ |
|---|---|---|---|
| 8-1 | H | Me | $OCH_2CH_2OMe$ |
| 8-2 | Me | Me | $OCH_2CH_2OMe$ |

TABLE 9

| No. | $^1$H-NMR δ ppm (Measuring instrument: JEOL-GSX(400 MHz)(Solvent: $CDCl_3$ unless otherwise specified, and the case where deuterated acetone was used, is identified as "in Acetone-d6") |
|---|---|
| 1-1 | 1.25(3H, t, J = 7.0 Hz), 1.76(3H, d, J = 5.2 Hz), 2.42(3H, s), 3.24(3H, s), 3.68(1H, q, J = 7.0 Hz), 3.69(3H, s), 3.72(3H, s), 4.99(2H, br s), 6.74(1H, q, J = 5.2 Hz), 7.26(1H, s), 7.42(1H, d, J = 8.0 Hz), 8.04(1H, d, J = 8.0 Hz). |
| 1-2 | 1.77(3H, d, J = 5.2 Hz), 2.32(3H, s), 3.18(3H, s), 3.69(3H, s), 3.71(3H, s), 3.98(3H, s), 6.73(1H, q, J = 5.2 Hz), 7.27(1H, s), 7.52(1H, d, J = 8.0 Hz), 7.94(1H, d, J = 8.0 Hz). |
| 1-3 | 1.77(3H, d, J = 5.2 Hz), 2.41(3H, s), 3.21(3H, s), 3.49(3H, s), 3.69(3H, s), 3.71(3H, s), 4.95(2H, br s), 6.74(1H, q, J = 5.2 Hz), 7.25(1H, s), 7.42(1H, d, J = 8.4 Hz), 8.04(1H, d, J = 8.4 Hz). |

TABLE 9-continued

| No. | $^1$H-NMR δ ppm (Measuring instrument: JEOL-GSX(400 MHz)(Solvent: CDCl$_3$ unless otherwise specified) |
|---|---|
| 1-4 | 1.24(6H, m), 1.76(3H, d, J = 5.6 Hz), 2.42(3H, s), 2.23(3H, s), 3.68(2H, q, J = 6.8 Hz), 3.69(3H, s), 4.11(2H, q, J = 7.2 Hz), 4.99(2H, br s), 6.73(1H, q, J = 5.6 Hz), 7.26(1H, s), 7.42(1H, d, J = 8.0 Hz), 8.04(1H, d, J = 8.0 Hz). |
| 1-5 | 1.19(6H, d, J = 6.0 Hz), 1.24(3H, t, J = 7.2 Hz), 1.76(3H, d, J = 5.2 Hz), 2.35(3H, s), 3.29(3H, s), 3.68(1H, m), 3.69(3H, s), 3.81(2H, m), 4.11(2H, q, J = 7.2 Hz), 4.21(2H, m), 6.70(1H, q, J = 5.2 Hz), 7.23(1H, d, J = 8.0 Hz), 7.28(1H, s), 7.87(1H, d, J = 8.0 Hz). |
| 1-6 | 1.44(3H, d, J = 6.4 Hz), 1.93(3H, s), 2.32(3H, s), 3.27(3H, s), 3.45(3H, s), 3.62(3H, s), 3.71(3H, s), 3.79(2H, t, J = 4.8 Hz), 4.22(2H, t, J = 4.8 Hz), 6.21(1H, q, J = 6.4 Hz), 7.20(1H, d, J = 8.0 Hz), 7.88(1H, d, J = 8.0 Hz). |
| 2-1 | 1.40(3H, t, J = 7.2 Hz), 1.77(3H, d, J = 5.2 Hz), 2.35(3H, s), 2.94(3H, s), 3.46(3H, s), 3.71(3H, s), 3.80(2H, t, J = 4.4 Hz), 4.05(2H, m), 4.24(2H, t, J = 4.4 Hz), 6.78(1H, q, J = 5.2 Hz), 7.26(1H, d, J = 7.6 Hz), 7.28(1H, s), 7.88(1H, d, J = 7.6 Hz). |
| 2-2 | 1.23(3H, t, J = 7.0 Hz), 1.40(3H, t, J = 7.4 Hz), 1.76(3H, d, J = 5.6 Hz), 2.33(3H, s), 3.18(3H, s), 3.97(3H, s), 4.0-4.1(4H, m), 6.79(1H, q, J = 5.6 Hz), 7.27(1H, s), 7.52(1H, d, J = 8.0 Hz), 7.94(1H, d, J = 8.0 Hz). |
| 2-3 | 1.18(3H, t, J = 7.2 Hz), 1.35(3H, t, J = 7.2 Hz), 1.96(3H, d, J = 5.2 Hz), 2.33(3H, s), 2.79(3H, s ), 3.35(3H, s), 3.42(3H, s), 3.80(2H, t, J = 4.4 Hz), 3.96(2H, q, J = 7.2 Hz), 4.10(2H, m), 4.25(2H, t, J = 4.4 Hz), 6.20(1H, q, J = 5.2 Hz), 7.30(1H, d, J = 7.6 Hz), 7.85(1H, d, J = 7.6 Hz) |

| No. | $^1$H-NMR δ ppm (Measuring instrument: JEOL-GSX(400 MHz)(Solvent: CDCl$_3$ unless otherwise specified) |
|---|---|
| 3-1 | 0.87(3H, t, J = 7.2 Hz), 1.19(3H, t, J = 7.2 Hz), 1.27(2H, m), 1.70(3H, d, J = 5.2 Hz), 2.33(3H, s), 3.32(3H, s), 3.41(3H, s), 3.80(2H, t, J = 7.2 Hz), 4.04(2H, q), 4.27(2H, q, J = 7.2 Hz), 6.77(1H, q, J = 5.2 Hz), 7.32(1H, d, J = 8 Hz), 7.38(1H, s), 7.83(1H, d, J = 8 Hz). |
| 4-1 | 1.40(3H, d, J = 6.4 Hz), 1.42(3H, d, J = 6.4 Hz), 1.77(3H, d, J = 5.2 Hz), 2.35(3H, s), 3.29(3H, s), 3.46(3H, s), 3.70(3H, s), 3.80(2H, t, J = 4.4 Hz), 4.24(2H, t, J = 4.4 Hz), 4.65(1H, m), 6.76(1H, q, J = 5.2 Hz), 7.26(1H, d, J = 8.4 Hz), 7.28(1H, s), 7.88(1H, d, J = 8.4 Hz). |
| 5-1 | 1.17(6H, d, J = 6.0 Hz), 2.38(3H, s), 3.33(3H, s), 3.67(3H, s), 3.69(1H, m), 3.84(2H, m), 3.23(2H, m), 7.44(1H, d, J = 8.4 Hz), 7.81(1H, s), 7.85(1H, d, J = 8.4 Hz). in Acetone-d$_6$ |
| 5-2 | 1.61(3H, s), 2.26(3H, s), 3.25(3H, s), 3.42(3H, s), 3.58(3H, s), 3.78(2H, t, J = 4.4 Hz), 4.19(2H, t, J = 4.4 Hz), 7.11(1H, d, J = 8.0 Hz), 7.87(1H, d, J = 8.0 Hz), 10.01(1H, bs). |
| 5-3 | 0.85(3H, t, J = 7.2 Hz), 1.99(2H, q, J = 7.2 Hz), 2.30(3H, s), 3.28(3H, s), 3.45(3H, s), 3.63(3H, s), 3.79(2H, t, J = 4.4 Hz), 4.22(2H, t, J = 4.4 Hz), 7.16(1H, d, J = 8.0 Hz), 7.90(1H, d, J = 8.0 Hz). |
| 6-1 | 1.35(3H, t, J = 7.2 Hz), 1.66(3H, s), 2.30(3H, s), 3.20(3H, s), 3.41(3H, s), 3.79(2H, t, J = 4.4 Hz), 3.97(2H, q, J = 7.2 Hz), 4.26(2H, t, J = 4.4 Hz), 7.30(1H, d, J = 8.0 Hz), 7.86(1H, d, J = 8.0). in Acetone-d$_6$ |
| 7-1 | 0.92(3H, t, J = 7.2 Hz), 1.56(3H, s), 1.84(2H, q, J = 7.2 Hz), 2.38(3H, s), 3.30(3H, s), 3.41(3H, s), 3.80(2H, t, J = 4.4 Hz), 3.97(2H, t, J = 7.2 Hz), 4.19(2H, t, J = 4.4 Hz), 7.40(1H, s), 7.46(1H, d, J = 7.2 Hz), 7.86(1H, d, J = 7.2 Hz). in Acetone-d$_6$ |
| 8-1 | 1.48(6H, d, J = 7.2 Hz), 2.40(3H, s), 3.30(3H, s), 3.46(3H, s), 3.80(2H, t, J = 4.4 Hz), 4.24(2H, t, J = 4.4 Hz), 4.57(1H, m), 7.34(1H, s), 7.36(1H, d, J = 8.0 Hz), 7.91(1H, d, J = 8.0 Hz) |
| 8-2 | 1.46(6H, d, J = 7.2 Hz), 1.67(3H, s), 2.32(3H, s), 3.29(3H, s), 3.46(3H, s), 3.79(2H, t, J = 4.4 Hz), 4.23(2H, t, J = 4.4 Hz), 4.54(1H, m), 7.16(1H, d, J = 8.0 Hz), 7.91(1H, d, J = 8.0 Hz). |

Now, Test Examples will be described.

Test Example 1

Upland field soil was put into a 1/170,000 hectare pot, and seeds of various plants were sown. When the respective plants reached predetermined leaf stage ((1) barnyardgrass (*Echinochloa crus-galli* L.): 1.2 to 3.0 leaf stage, (2) crabgrass (*Digitaria sanguinalis* L.): 1.0 to 3.0 leaf stage, (3) green foxtail (*Setaria viridis* L.): 1.5 to 3.0 leaf stage, (4) redroot pigweed (*Amaranthus retroflexus* L.): cotyledon stage to 1.5 leaf stage, (5) prickly *sida* (*Sida spinosa* L.): cotyledon stage to 2.0 leaf stage, (6) velvetleaf (*Abutilon theophrasti* MEDIC.): cotyledon stage to 1.3 leaf stage, (7) rice (*Oryza sativa* L.): 1.2 to 2.5 leaf stage, (8) corn (*Zea mays* L.): 2.0 to 3.3 leaf stage, (9) soybean (*Glycine max* Merr.): primary leaf stage to 0.3 leaf stage) and wheat (*Triticum* spp.): 2.0 to 3.0 leaf stage, wettable powders or emulsifiable concentrates of the compounds of the present invention prepared in accordance with a conventional preparation method, were weighed so that the active ingredients became the prescribed amounts, and diluted with water in an amount corresponding to 500 liter per 1 hectare (containing 0.1 vol % of an agricultural spreader ("KUSARINOH", manufactured by NIHON NOHYAKU CO., LTD.)). The spray solutions thus prepared were applied for foliar treatment by a small sprayer.

On the 20th to 22nd day after application, the state of growth of the respective plants was visually observed, and the herbicidal effect was evaluated by a growth inhibition rate (%) of 0 (equivalent to the non-treated area) to 100% (complete kill). The results are shown in Table 10.

TABLE 10

| Compound No. | Amount of active ingredient (g/ha) | Growth inhibition rate (%) | | | | | | | | | | Date of observation |
|---|---|---|---|---|---|---|---|---|---|---|---|---|
| | | Barnyardgrass | Crabgrass | Green foxtail | Redroot pigweed | Prickly sida | Velvetleaf | Rice | Corn | Soybean | Wheat | |
| 1-1 | 7 | 95 | 90 | 60 | 60 | — | 50 | 20 | — | 70 | 0 | 21 |
| 1-2 | 7 | 100 | 90 | 100 | 95 | — | 80 | 70 | 0 | 95 | 0 | 21 |
| 1-3 | 7 | 90 | 95 | 80 | 80 | — | 75 | 60 | — | 70 | 0 | 21 |
| 1-4 | 7 | 95 | 95 | 75 | 80 | — | 80 | — | 0 | 80 | 0 | 21 |
| 1-5 | 7 | 95 | 90 | 80 | 80 | 0 | 80 | 20 | 10 | — | 0 | 21 |
| 1-6 | 7 | 90 | 90 | 95 | 90 | 70 | 98 | 70 | 0 | 80 | 0 | 20 |
| 2-1 | 7 | 95 | 100 | 100 | 90 | 60 | 100 | 70 | 0 | 95 | 0 | 20 |
| 2-2 | 7 | 98 | 80 | 80 | 98 | 70 | 95 | 50 | 0 | — | 0 | 22 |
| 3-1 | 7 | 70 | 70 | 30 | 80 | 0 | 60 | 0 | 0 | — | 0 | 22 |
| 4-1 | 7 | 90 | 90 | 95 | 85 | 60 | 100 | 80 | 0 | 95 | 0 | 20 |
| 5-1 | 7 | 30 | 50 | 50 | 60 | 40 | 10 | 0 | 0 | — | 0 | 22 |
| 5-2 | 7 | 90 | 90 | 100 | 90 | 40 | 70 | 50 | 0 | 70 | — | 21 |
| 5-3 | 7 | 90 | 90 | 90 | 95 | 30 | 80 | 50 | 0 | 0 | — | 21 |
| 6-1 | 7 | 10 | 50 | 60 | 60 | 0 | 50 | 20 | 0 | — | 0 | 22 |
| 7-1 | 7 | 60 | 70 | 70 | 70 | 20 | 75 | 10 | 0 | 60 | 0 | 22 |
| 8-1 | 7 | 60 | 95 | 90 | 90 | 30 | 80 | 10 | 0 | 40 | 0 | 21 |
| 8-2 | 7 | 20 | 40 | 50 | 60 | 20 | 60 | 0 | 0 | 10 | 0 | 21 |

Test Example 2

Upland field soil was put into a 1/170,000 hectare pot, and seeds of various plants (barnyardgrass (*Echinochloa crusgalli* L.), crabgrass (*Digitaria sanquinalis* L.), green foxtail (*Setaria viridis* L.), redroot pigweed (*Amaranthus retroflexus* L.), prickly sida (*Sida spinosa* L.), velvetleaf (*Abutilon theophrasti* MEDIC.), rice (*Oryza sativa* L.), corn (*Zea mays* L.), soybean (*Glycine max* Merr.)) and wheat (*Triticum* spp.) were sown. On the day after sowing, wettable powders or emulsifiable concentrates of the compounds of the present invention prepared in accordance with a conventional preparation method, were weighed so that the active ingredients became the prescribed amounts, and diluted with water in an amount corresponding to 500 liter per 1 hectare, followed by soil application with a small sprayer.

On the 21st to 22nd day after the application, the state of growth of the respective plants was visually observed, and the herbicidal effect was evaluated by a growth inhibition rate (%) of from 0 (equivalent to the non-treated area) to 100% (complete kill). The results are shown in Table 11.

Test Example 3

Paddy field soil was put into a 1/1,000,000 hectare pot, and seeds of barnyardgrass (*Echinochloa oryzicola* vasing.) and Japanese bulrush (*Scirpus juncoides*) were sown and lightly covered with soil. Then, pot was left to stand in a greenhouse in a state irrigated to a water depth of from 0.5 to 1 cm, and next day or two days later, tubers of Japanese ribbon waparo (*Sagittaria pygmaea*) were planted. Then, the irrigated water depth was maintained to be from 3 to 4 cm, and when barnyardgrass and Japanese bulrush reached 0.5 leaf stage, and Japanese ribbon waparo reached primary leaf stage, a water diluted solution of a wettable powder or an emulsifiable concentrate of the compound of the present invention prepared in accordance with a conventional preparation method, was uniformly dropwise applied by a pipette so that the amount of active ingredients would be a prescribed amount. Further, paddy field soil was put into a 1/1,000,000 pot, followed by soil puddling to an irrigated water depth of from 3 to 4 cm. Next day, rice (*Oryza sativa* L.) (var.: Nihonbare) of two leaf stage was transplanted in a transplantation depth of 3 cm. On

TABLE 11

| Compound No. | Amount of active ingredient (g/ha) | Growth inhibition rate (%) | | | | | | | | | | Date of observation |
|---|---|---|---|---|---|---|---|---|---|---|---|---|
| | | Barnyardgrass | Crabgrass | Green foxtail | Redroot pigweed | Prickly sida | Velvetleaf | Rice | Corn | Soybean | Wheat | |
| 1-1 | 250 | 100 | 100 | 98 | 90 | 90 | 98 | 95 | 10 | 20 | 20 | 21 |
| 1-2 | 250 | 100 | 100 | 100 | 100 | 98 | 100 | 100 | 0 | 70 | 20 | 21 |
| 1-3 | 250 | 98 | 98 | 98 | 98 | 95 | 100 | 98 | 20 | 60 | 10 | 21 |
| 1-4 | 250 | 98 | 80 | 80 | 98 | 90 | 100 | 60 | 0 | 40 | 0 | 21 |
| 1-5 | 250 | 100 | 95 | 100 | 100 | 90 | 100 | 80 | 10 | 10 | 0 | 21 |
| 1-6 | 250 | 100 | 100 | 70 | 100 | 99 | 100 | 98 | 0 | 0 | 5 | 21 |
| 2-1 | 250 | 95 | 100 | 100 | 100 | 90 | 100 | 98 | 0 | 0 | 0 | 21 |
| 3-1 | 250 | 60 | 80 | 60 | 40 | 80 | 80 | 20 | 0 | 0 | 10 | 21 |
| 4-1 | 250 | 100 | 100 | 100 | 100 | 95 | 100 | 98 | 0 | 0 | 10 | 21 |
| 5-1 | 250 | 98 | 98 | 95 | 100 | 98 | 100 | 98 | 10 | 0 | 20 | 21 |
| 5-2 | 250 | 10 | 100 | 60 | 90 | 0 | 70 | 10 | 0 | 20 | 0 | 21 |
| 5-3 | 250 | 50 | 95 | 60 | 100 | 20 | 30 | 20 | 20 | 0 | 0 | 21 |
| 6-1 | 250 | 100 | 100 | 98 | 100 | 80 | 80 | 100 | 0 | 60 | 20 | 21 |
| 7-1 | 250 | 98 | 100 | 90 | 100 | 80 | 95 | 98 | 0 | 20 | 40 | 21 |
| 8-1 | 250 | 100 | 100 | 100 | 100 | 40 | 100 | 80 | 0 | 0 | 0 | 21 |
| 8-2 | 250 | 100 | 100 | 100 | 100 | 60 | 70 | 100 | 60 | — | 20 | 22 | the 4th day after transplantation, the compound of the present invention was applied in the same manner as described above.

On the 13th to 17th day after application, the state of growth of barnyardgrass, Japanese bulrush and Japanese ribbon waparo was visually observed, and on the 20th to 23rd day after application, the state of growth of rice was visually observed, and the herbicidal effect was evaluated by a growth inhibition rate (%) of 0 (equivalent to the non-treated area) to 100% (complete kill). The results are shown in Table 12.

TABLE 12

| Compound No. | Amount of active ingredient (g/ha) | Growth inhibition rate (%) | | | |
|---|---|---|---|---|---|
| | | barnyard grass | Japanese bulrush | Japanese ribbon waparo | Rice |
| 1-1 | 63 | 100 | 70 | 90 | 10 |
| 1-2 | 63 | 100 | 70 | 95 | 40 |
| 1-3 | 63 | 100 | 70 | 70 | 40 |
| 1-4 | 63 | 100 | 60 | 70 | 20 |
| 1-5 | 63 | 100 | 20 | 90 | 30 |
| 1-6 | 63 | 100 | 70 | 60 | 30 |
| 2-1 | 63 | 100 | 80 | 80 | 20 |
| 2-2 | 63 | 100 | 80 | 90 | 80 |
| 3-1 | 63 | 100 | 90 | 95 | 30 |
| 4-1 | 63 | 100 | 98 | 70 | 40 |
| 5-1 | 63 | 60 | 20 | 95 | 30 |
| 5-2 | 63 | 80 | 70 | 80 | 20 |
| 5-3 | 63 | 60 | 50 | 50 | 20 |
| 6-1 | 63 | 60 | 80 | 60 | 40 |
| 7-1 | 63 | 30 | 70 | 90 | 20 |
| 8-1 | 63 | 95 | 95 | 95 | 60 |
| 8-2 | 63 | 40 | 70 | — | 10 |

Test Example 4

Upland field soil is put into a 1/1,000,000 hectare pot, and seeds of various plants are sown. When the respective plants reach predetermined leaf stage ((1) velvetleaf (*Abutilon theophrasti* MEDIC.), (2) guineagrass (Panicum maximum Jacq.), (3) green foxtail (*Setaria viridis* L.), and (4) corn (*Zea mays* L.), a wettable powder of compound No. 2-1 of the above-mentioned present invention, an emulsifiable concentrate of the following Reference Compound 1 and a wettable powder of the following Reference Compound 2, prepared in accordance with a conventional preparation method, are weighed so that the active ingredients become the prescribed amounts 3.5 to 15 g/ha, and diluted with water in an amount corresponding to 300 liter per 1 hectare (containing 0.5 vol % of an agricultural spreader (MSO concentrate, manufactured by Cognis Corporation). The spray solutions thus prepared are applied for foliar treatment by a small sprayer.

On the 14th to 28th day after application, the state of growth of the respective plants is visually observed, and the herbicidal effect is evaluated by a growth inhibition rate (%) of 0 (equivalent to the non-treated area) to 100% (complete kill). Compound No. 2-1 of the present invention shows superior herbicidal effects and excellent safety to crop plants as compared to the following Reference Compounds.

Reference Compound 1:

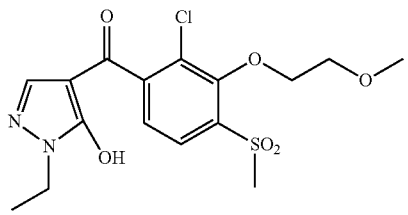 [SMILES: CCn1ncc(C(=O)c2ccc(S(C)(=O)=O)c(OCCOC)c2Cl)c1O]

(Compound No. 1 Disclosed at Page 18 of EP0352543A1)

Reference Compound 2:

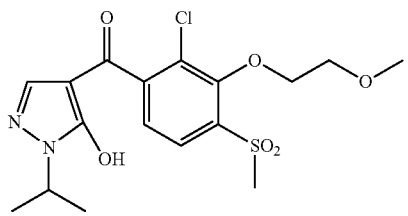 [SMILES: COCCOc1c(S(C)(=O)=O)ccc(C(=O)c2cnn(C(C)C)c2O)c1Cl]

(Compound No. 20 disclosed at page 21 of EP0352543A1)

Test Example 5

Upland field soil was put into a 1/1,000,000 hectare pot, and seeds of various plants were sown. When the respective plants reached predetermined leaf stage ((1) velvetleaf (*Abutilon theophrasti* MEDIC.): 3.0 to 3.5 leaf stage, (2) giant foxtail (*Setaria faberi* Herrm.): 4.0 to 4.5 leaf stage, (3) green foxtail (*Setaria viridis* L.): 5.0 to 5.5 leaf stage, and (4) corn (*Zea mays* L.): 4.0 to 4.3 leaf stage, a wettable powder of compound No. 2-1 of the above-mentioned present invention, a wettable powder of the above-mentioned Reference Compound 1 and a wettable powder of the above-mentioned Reference Compound 2, prepared in accordance with a conventional preparation method, were weighed so that the active ingredients became the prescribed amounts, and diluted with water in an amount corresponding to 300 liter per 1 hectare (containing 0.5 vol % of an agricultural spreader (Destiny HC: WINFIELD SOLUTIONS by LLC). The spray solutions thus prepared were applied for foliar treatment by a small sprayer.

On the 7th to 20th day after application, the state of growth of the respective plants was visually observed, and the herbicidal effect was evaluated by a growth inhibition rate (%) of 0 (equivalent to the non-treated area) to 100% (complete kill). The results are shown in Tables 13 to 16.

TABLE 13

| Compound No. | Amount of active ingredient (g/ha) | Growth inhibition rate (%) (20th day after application) Velvet leaf |
|---|---|---|
| 2-1 | 3.5 | 80 |
| Reference Compound 1 | 3.5 | 45 |
| Reference Compound 2 | 3.5 | 50 |

TABLE 14

| Compound No. | Amount of active ingredient (g/ha) | Growth inhibition rate (%) (20th day after application) Giant foxtail |
|---|---|---|
| 2-1 | 3.5 | 83 |
| Reference Compound 1 | 3.5 | 30 |
| Reference Compound 2 | 3.5 | 0 |

TABLE 15

| Compound No. | Amount of active ingredient (g/ha) | Growth inhibition rate (%) (18th day after application) Green foxtail |
|---|---|---|
| 2-1 | 7 | 70 |
| Reference Compound 1 | 7 | 40 |
| Reference Compound 2 | 7 | 35 |

TABLE 16

| Compound No. | Amount of active ingredient (g/ha) | Growth inhibition rate (%) (7th day after application) Corn |
|---|---|---|
| 2-1 | 90 | 0 |
| Reference Compound 2 | 90 | 25 |

Test Example 6

Soil (sterilized soil:sand=3:1) was packed (4 L) into a column (9.5 cm in diameter×40 cm in height, application area: 0.007 m²), and tap water was dropped from above by a Peristaltic pump before application of the herbicide for the purpose of maintaining the soil moisture to be uniform. Then, 10 mL of a spray solution prepared so that each agent (Compound No. 2-1, the above Reference Compounds 1 and 2) would be at a concentration corresponding to 250 g/ha was dropwise applied by a pipette. After application, water was dropped again at a rate of 400 mL/hr for about 3 hours by means of a Peristaltic pump. After the dropping, the column was left to stand for 1 day, and then the column was vertically evenly divided and seeds of sorgo (*Sorghum bicolor* Moench) (var.: Lucky Sorgo) were sown in a row. On the 14th day after sowing, the state of growth of the plant was visually observed at 3 cm intervals from the application point of the agent, whereby the germination and the degree of growth were evaluated by a growth inhibition rate (%) of 0 (equivalent to the non-treated area) to 100% (complete kill) to obtain the results in Table 17.

TABLE 17

Growth inhibition rate (%) against sorgo

| Active ingredient | Depth (cm) from the applied surface | | | | | | | | | |
|---|---|---|---|---|---|---|---|---|---|---|
| | 0-3 | 3-6 | 6-9 | 9-12 | 12-15 | 15-18 | 18-21 | 21-24 | 24-27 | 27-30 |
| Compound No. 2-1 | 70 | 19 | 10 | 5 | 3 | 3 | 2 | 1 | 0 | 0 |
| Reference Compound No. 1 | 58 | 58 | 58 | 60 | 53 | 35 | 28 | 30 | 28 | 15 |
| Reference Compound No. 2 | 48 | 45 | 47 | 43 | 58 | 55 | 61 | 63 | 35 | 8 |

From the above results, the growth inhibition rates of Reference Compounds No. 1 and No. 2 are observed in depths deeper than that of Compound No. 2-1. Thus, it is evident that with Reference Compounds No. 1 and No. 2, the active ingredient moved to deeper depths. Whereas, Compound No. 2-1 stayed at a shallow portion of soil (in a layer of from 0 to 9 cm). From such results, Compound No. 2-1 is considered to be an excellent compound which is scarcely moved downward from the applied portion by e.g. raining or water spraying and whereby the possibility influential over the environment such as contamination of underground water is extremely low as compared with Reference Compounds No. 1 and No. 2.

Now, Formulation Examples of the present invention will be described.

Formulation Example 1

| | |
|---|---|
| (1) The compound of the present invention | 75 parts by weight |
| (2) Geropon T-77 (tradename, manufactured by Rhone-Poulenc) | 14.5 parts by weight |
| 3) NaCl | 10 parts by weight |
| 4) Dextrin | 0.5 part by weight |

The above components are placed in a high-speed mixing granulator, admixed with 20 wt % of water, granulated, and dried to obtain water-dispersible granules.

Formulation Example 2

| | |
|---|---|
| (1) Kaolin | 78 parts by weight |
| (2) Laveline FAN (tradename, manufactured by DAI-ICHI KOGYO SEIYAKU CO., LTD.) | 2 parts by weight |
| (3) Sorpol 5039 (tradename, manufactured by TOHO Chemical Industry Co., Ltd.) | 5 parts by weight |
| (4) Carplex (tradename, manufactured by DSL. Japan Co., Ltd.) | 15 parts by weight |

The mixture of the above components (1) to (4) and the compound of the present invention are mixed in a weight ratio of 9:1 to obtain a wettable powder.

Formulation Example 3

| | |
|---|---|
| (1) Hi-Filler No. 10 (tradename, manufactured by Matsumura Sangyo Co., Ltd.) | 33 parts by weight |
| (2) Sorpol 5050 (tradename, manufactured by TOHO Chemical Industry Co., Ltd.) | 3 parts by weight |

-continued

| | |
|---|---|
| (3) Sorpol 5073 (tradename, manufactured by TOHO Chemical Industry Co., Ltd.) | 4 parts by weight |
| (4) The compound of the present invention | 60 parts by weight |

The above compounds (1) to (4) are mixed to obtain a wettable powder.

Formulation Example 4

| | |
|---|---|
| (1) The compound of the present invention | 4 parts by weight |
| (2) Bentonite | 30 parts by weight |
| (3) Calcium carbonate | 61.5 parts by weight |
| (4) Toxanon GR-31A (tradename, manufactured by Sanyo Chemical Industries Co., Ltd.) | 3 parts by weight |
| (5) Calcium lignin sulfonate | 1.5 parts by weight |

Pulverized component (1) and components (2) and (3) are preliminarily mixed, and then components (4) and (5) and water are mixed thereto. The mixture is extruded and granulated, followed by drying and sieving to obtain granules.

Formulation Example 5

| | |
|---|---|
| (1) The compound of the present invention | 30 parts by weight |
| (2) Zieclite (tradename, manufactured by Zieclite Co., Ltd.) | 60 parts by weight |
| (3) New Kalgen WG-1 (tradename, manufactured by TAKEMOTO OIL & FAT CO., LTD.) | 5 parts by weight |
| (4) New Kalgen FS-7 (tradename, manufactured by TAKEMOTO OIL & FAT CO., LTD.) | 5 parts by weight |

Components (1), (2) and (3) are mixed and passed through a pulverizer, and then component (4) is added thereto. The mixture is kneaded and then extruded and granulated, followed by drying and sieving to obtain water dispersible granules.

Formulation Example 6

| | |
|---|---|
| (1) The compound of the present invention | 28 parts by weight |
| (2) Soprophor FL (tradename, manufactured by Rhone-Poulenc) | 2 parts by weight |
| (3) Sorpol 335 (tradename, manufactured by TOHO Chemical Industry Co., Ltd.) | 1 part by weight |
| (4) IP solvent 1620 (tradename, manufactured by Idemitsu Petrochemical Co., Ltd.) | 32 parts by weight |
| (5) Ethylene glycol | 6 parts by weight |
| (6) Water | 31 parts by weight |

The above components (1) to (6) are mixed and pulverized by a wet-grinding machine (Dyno-mill) to obtain a water-based suspension concentrate.

The entire disclosures of Japanese Patent Application No. 2008-132190 filed on May 20, 2008 and Japanese Patent Application No. 2009-003467 filed on Jan. 9, 2009 including specifications, claims and summaries are incorporated herein by reference in their entireties.

The invention claimed is:

1. A pyrazole compound represented by the formula (I) or its salt:

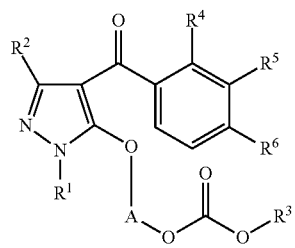

(I)

wherein $R^1$ is alkyl, $R^2$ is a hydrogen atom or alkyl, $R^3$ is alkyl, $R^4$ is alkyl, $R^5$ is alkyl substituted by one alkoxy, alkoxy substituted by one alkoxy, or alkoxycarbonyl, $R^6$ is alkylsulfonyl, A is alkylene substituted by at least one alkyl.

2. The pyrazole compound or its salt according to claim 1, wherein the pyrazole compound represented by the formula (I) is 1-(4-(3-(ethoxymethyl)-2-methyl-4-(methyl sulfonyl)benzoyl)-1-methyl-1H-pyrazol-5-yloxy)ethyl methyl carbonate, methyl 3-(5-(1-(methoxycarbonyloxy)ethoxy)-1-methyl-1H-pyrazole-4-carbonyl)-2-methyl-6-(methylsulfonyl)benzoate, 1-(4-(3-(methoxymethyl)-2-methyl-4-(methylsulfonyl)benzoyl)-1-methyl-1H-pyrazol-5-yloxy)ethyl methyl carbonate, 1-(4-(3-(ethoxymethyl)-2-methyl-4-(methylsulfonyl)benzoyl)-1-methyl-1H-pyrazol-5-yloxy)ethyl ethyl carbonate, ethyl 1-(4-(3-(2-isopropoxyethoxy)-2-methyl-4-(methyl sulfonyl)benzoyl)-1-methyl-1H-pyrazol-5-yloxy)ethyl carbonate, 1-(4-(3-(2-methoxyethoxy)-2-methyl-4-(methylsulfonyl)benzoyl)-1,3-dimethyl-1H-pyrazol-5-yloxy)ethyl methyl carbonate, 1-(1-ethyl-4-(3-(2-methoxyethoxy)-2-methyl-4-(methylsulfonyl)benzoyl)-1H-pyrazol-5-yloxy)ethyl methyl carbonate, methyl 3-(5-(1-(ethoxycarbonyloxy)ethoxy)-1-ethyl-1H-pyrazole-4-carbonyl)-2-methyl-6-(methylsulfonyl)benzoate, ethyl 1-(1-ethyl-4-(3-(2-methoxyethoxy)-2-methyl-4-(methylsulfonyl)benzoyl)-3-methyl-1H-pyrazol-5-yloxy)ethyl carbonate, ethyl 1-(1-n-propyl-4-(3-(2-methoxyethoxy)-2-methyl-4-(methylsulfonyl)benzoyl)-1H-pyrazol-5-yloxy)ethyl carbonate, or 1-(1-isopropyl-4-(3-(2-methoxyethoxy)-2-methyl-4-(methylsulfonyl)benzoyl)-1H-pyrazol-5-yloxy)ethyl methyl carbonate.

3. The pyrazole compound or its salt according to claim 1, wherein the pyrazole compound represented by the formula (I) is 1-(1-ethyl-4-(3-(2-methoxyethoxy)-2-methyl-4-(methylsulfonyl)benzoyl)-1H-pyrazol-5-yloxy)ethyl methyl carbonate.

4. A process for producing a pyrazole compound represented by the formula (I) or its salt:

(I)

wherein $R^1$ is alkyl, $R^2$ is a hydrogen atom or alkyl, $R^3$ is alkyl, $R^4$ is alkyl, $R^5$ is alkyl substituted by one alkoxy, alkoxy substituted by one alkoxy, or alkoxycarbonyl, $R^6$ is alkylsulfonyl, A is alkylene substituted by at least one alkyl, which comprises reacting a pyrazole compound represented by the formula (II) or its salt:

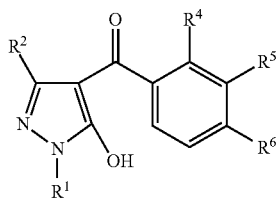

(II)

wherein $R^1$, $R^2$, $R^4$, $R^5$ and $R^6$ are as defined above, with a compound represented by the formula (III):

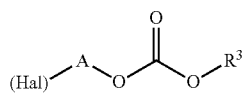

(III)

wherein Hal is halogen, and $R^3$ and A are as defined above.

5. A herbicide containing the pyrazole compound or its salt as defined in claim 1 as an active ingredient.

6. A method for controlling undesired plants or inhibiting their growth, which comprises applying a herbicidally effective amount of the pyrazole compound or its salt as defined in claim 1, to the undesired plants or to a place where they grow.

7. The method of claim 6, wherein the undesired plant is at least one selected from the group consisting of gramineae, cyperaceae, alismataceae, pontederiaceae, scrophulariaceae, lythraceae, elatinaceae, malvaceae, compositae, solanaceae, amaranthaceae, polygonaceeae, cruciferae, convolvulaceae, Chenopodiaceae, Portulacaceae, leguminosae, caryophyllaceae, labiatae, rubiaceae, euphorbiaceae, and Commelinaceae.

8. A method for controlling undesired plants or inhibiting their growth, which comprises applying a herbicidally effective amount of the pyrazole compound or its salt as defined in claim 1 to at least one crop selected from the group consisting of corn (*Zea mays* L.), soybean (*Glycine max* Men.), cotton (*Gossypium* spp.), wheat (*Triticum* spp.), rice (*Oryza sativa* L.), barley (*Hordeum vulgare* L.), rye (*Secale cereale* L.), oat (*Avena sativa* L.), sorgo (*Sorghum bicolor* Moench), rape (*Brassica napus* L.), sunflower (*Helianthus annuus* L.), sugar beet (*Beta vulgaris* L.), sugar cane (*Saccharum officinarum* L.), japanese lawngrass (*Zoysia japonica stend*), peanut (*Arachis hypogaea* L.), flax (*Linum usitatissimum* L.), tobacco (*Nicotiana tabacum* L.), and coffee (*Coffea* spp.).

9. The method of claim 6, wherein the herbicidally effective amount of the pyrazole compound is applied in the form of dust, a granule, a water dispersible granule, a wettable powder, a tablet, a pill, a capsule, a water-based suspension, an oil-based suspension, a microemulsion, a suspoemulsion, a water soluble powder, an emulsifiable concentrate, a soluble concentrate and a paste.

10. The method of claim 9, wherein the herbicidally effective amount of the pyrazole compound is mixed with an additive selected from the group consisting of a solid carrier, a solvent, an anionic surfactant, a nonionic surfactant, a vegetable oil and a mineral oil.

11. The method of claim 6, wherein the pyrazole compound is applied in an amount of from 0.1 to 5,000 g per hectare of the undesired plants or to the place where they grow.

12. The method of claim 6, wherein the pyrazole compound is applied in an amount of from 0.5 to 1,000 g per hectare of the undesired plants or to the place where they grow.

13. The method of claim 6, wherein the pyrazole compound is applied in an amount of from 1 to 500 g per hectare of the undesired plants or to the place where they grow.

14. The method of claim 8, wherein the pyrazole compound is applied in an amount of from 0.1 to 5,000 g per hectare of the crop.

15. The method of claim 8, wherein the pyrazole compound is applied in an amount of from 0.5 to 1,000 g per hectare of the crop.

16. The method of claim 8, wherein the pyrazole compound is applied in an amount of from 1 to 500 g per hectare of the crop.

* * * * *